United States Patent
Tang et al.

(10) Patent No.: US 10,380,737 B2
(45) Date of Patent: Aug. 13, 2019

(54) DETECTION OF MICROANEURYSMS

(71) Applicant: UNIVERSITY OF SURREY, Surrey (GB)

(72) Inventors: Hongying Lilian Tang, Surrey (GB); Su Wang, Surrey (GB)

(73) Assignee: UNIVERSITY OF SURREY, Surrey (GB)

( * ) Notice: Subject to any disclaimer, the term of this patent is extended or adjusted under 35 U.S.C. 154(b) by 0 days.

(21) Appl. No.: 15/551,240

(22) PCT Filed: Feb. 16, 2016

(86) PCT No.: PCT/GB2016/050381
§ 371 (c)(1),
(2) Date: Aug. 15, 2017

(87) PCT Pub. No.: WO2016/132115
PCT Pub. Date: Aug. 25, 2016

(65) Prior Publication Data
US 2018/0068440 A1  Mar. 8, 2018

Related U.S. Application Data

(60) Provisional application No. 62/116,588, filed on Feb. 16, 2015.

(51) Int. Cl.
G06T 7/00 (2017.01)
A61B 3/00 (2006.01)
A61B 3/12 (2006.01)

(52) U.S. Cl.
CPC .......... *G06T 7/0012* (2013.01); *A61B 3/0016* (2013.01); *A61B 3/12* (2013.01); *G06T 2207/20076* (2013.01); *G06T 2207/20081* (2013.01); *G06T 2207/30041* (2013.01)

(58) Field of Classification Search
None
See application file for complete search history.

(56) References Cited

U.S. PATENT DOCUMENTS

2012/0177262 A1* 7/2012 Bhuiyan .............. A61B 3/0025
382/128

OTHER PUBLICATIONS

Lazar et al., "A Novel Approach for the Automatic Detection of Microaneurysms in Retinal Images", 2010 6th International Conference on Emerging Technologies.*
(Continued)

*Primary Examiner* — Matthew C Bella
*Assistant Examiner* — Brian D Shin
(74) *Attorney, Agent, or Firm* — Chang & Hale LLP

(57) ABSTRACT

An image analysis method and an image processing apparatus are disclosed. The image analysis method comprises receiving a retinal image and identifying at least one candidate object from a plurality of objects within the retinal image. Singular spectrum analysis SSA is performed on the at least one candidate object, to obtain an intensity profile along at least one cross-sectional line through the candidate object. At least one feature from the intensity profile is extracted for classification of the at least one candidate object.

20 Claims, 16 Drawing Sheets

(56) References Cited

OTHER PUBLICATIONS

International Search Report and Written Opinion for PCT/GB2016/050381 dated May 17, 2016.
Istvan Lazar et al., "Microaneurysm detection in retinal images using a rotating cross-section based model," 2011 8th IEEE International Symposium on Biomedical Imaging: From Nano to Macro (ISBI 2011), IEEE, United States, Mar. 30, 2011, pp. 1405-1409.

\* cited by examiner

DETECTION OF MICROANEURYSMS

FIELD

The present invention relates to an image analysis method and apparatus. Particularly, the present invention relates to the analysis of retinal images.

BACKGROUND

Reliable recognition of microaneurysms is an essential task when designing an automated analysis system for digital colour fundus images. In this work, we propose an integrated approach for automated microaneurysm detection with high accuracy.

Diabetic retinopathy (DR) is the most common microvascular complication of diabetes and remains the leading cause of vision loss in the working-age population. Early diagnosis through regular screening helps prevent vision loss. In a DR screening programme, a large number of digital retinal images need to be examined for the presence of DR by human experts. Pathological signs of DR in the digital colour fundus images are dark lesions including microaneurysms (MAs) and haemorrhages, as well as bright lesions such as exudates and cotton wool spots. FIG. 1 shows an instance of digital fundus image that contains both anatomic structures (Optic Disc, Macula and Blood Vessels) and pathological signs of DR (MAs, haemorrhage, and exudates). White boxes indicate some of the MAs.

An automated system for separating healthy and diseased regions in the image can efficiently reduce the workload associated with large scale screening. Over the last two decades, research in DR image analysis has been constantly increasing. Studies of automated DR screening systems have appeared in the literature. One critical stage in these automated image processing systems is microaneurysm detection.

MAs are the first visible signs of DR and they appear as small circular reddish dots in the retina. The quantity of MAs indicates the progression of DR. The complexity of MA recognition lies in the fact that MAs can be located anywhere in the retina: in isolation, in clusters, close to vasculature, around macula or among exudates. Meanwhile, their local contrast is very low compared to their surrounding background and their edges are not well defined in the image.

In addition, MAs have very similar intensity and morphological characteristics to other DR signs and anatomical features such as haemorrhages, thin vessel junctions, visually disconnected vessel fragments, local darkenings on the vessels or retinal background noise. FIGS. 2a to 2c show examples of some challenging cases for detecting MAs. Here, FIG. 2a shows a subtle MA, FIG. 2b shows an MA close to the vasculature, and FIG. 2c shows the vessel crossing that is similar to MAs.

Retinal images of patients from different ethnic groups also pose challenges for MA detection by varying background colour, introducing new disease patterns and often new non-DR diseases that are unknown to the automated system. FIG. 3 shows the retinal images from different populations. The first row shows the retinal images from different populations: (a) Kenya, (b) Botswana, (c) Mongolia, (d) China, (e) Saudi Arabia, (f) Italy, (g), Lithuania and (h) Norway. The second row shows the corresponding detailed subimages in the white boxes in the first row. Note that the images shown here were preprocessed by removing the black borders around the field of view. All images have been scaled to equal height for display.

Therefore, the present invention provides an automated system to recognise MAs in large scale fundus images with clinically acceptable accuracy regardless of their quality, ethnic origins and the type of camera used.

One exemplary prior art method applied a template-matching method to detect MAs in the wavelet domain. The authors considered that the wavelets could be effectively used to distinguish between lesions and non-lesion areas. The MAs were modelled with a 2D rotation-symmetric generalised Gaussian function, and the optimal adapted wavelet transform for MA detection was obtained by applying the lifting scheme framework. MAs were validated by applying a threshold on the matching result. The method of the present invention is focused on analysing the intensity profiles of MAs.

An intensity profile is a sequence of pixel intensities when scanning an image along certain direction. As the intensity profiles across MA objects have local minima, they can be modelled as an inverted 2D Gaussian shape. An understanding of the intensity profiles of an MA in an image plays an important role for an effective separation between the MA and other similar objects. A few methods following this approach for MA detection have been proposed by several authors. In one exemplary work, the cross-section profiles were extracted by detecting the local maximum pixels in an inverted image. A naïve Bayes (NB) classification was then used to remove false MA candidates based on a set of statistical measures of cross-section profiles, including the size, height and shape of the directional cross-sections of MAs.

Although these reported MA extraction approaches have some advantages, they still have difficulty in extracting MAs that are located close to blood vessels and discriminating MAs from the most common interfering structures such as vessel crossings and elongated haemorrhages.

SUMMARY

According to a first aspect of the present invention, there is provided an image analysis method, comprising: receiving a retinal image; identifying at least one candidate object from a plurality of objects within the retinal image; performing singular spectrum analysis SSA on the at least one candidate object, to obtain an intensity profile along at least one cross-sectional line through the candidate object; and extracting at least one feature from the intensity profile for classification.

Identifying the at least one candidate object may comprise dark object extraction through measuring connected neighbourhood strengths.

Identifying the at least one candidate object may further comprise eliminating spurious candidate objects using thresholding confidence maps.

The method may further comprise pre-processing the image of the retina, wherein pre-processing comprises applying a filter to remove bright lesions. The filter may be a Gaussian filter.

The at least one candidate object may comprise at least one of a microaneurysm MA, a blood vessel, a haemorrhage, or a scar.

If the at least one candidate object comprises an MA, the at least one cross-sectional line comprises a plurality of cross-sectional lines spreading radially from the centre of the candidate object.

The method may further comprise adjusting the at least one intensity profile of the candidate object by a correlation coefficient between the profile and a typical MA profile to obtain at least one scaled intensity profile for the candidate object.

Extracting at least one feature may comprise measuring at least one of: the mean of a peak width; standard deviation of the peak width; the mean of the heights of decreasing slopes of scaled intensity profiles along a plurality of cross-sectional lines through the candidate object; the standard deviation of decreasing slopes of scaled intensity profiles along a plurality of cross-sectional lines through the candidate object; the mean of the heights of increasing slopes of scaled intensity profiles along a plurality of cross-sectional lines through the candidate object; the standard deviation of the heights of increasing slopes of scaled intensity profiles along a plurality of cross-sectional lines through the candidate object; the compactness of the candidate object; the mean of the largest eigenvalues of scaled intensity profiles along a plurality of cross-sectional lines through the candidate object; the standard deviation of the largest eigenvalues of scaled intensity profiles along a plurality of cross-sectional lines through the candidate object; the mean of the aspect ratio; and the standard deviation of the aspect ratio.

The method may comprise classifying the at least one candidate object as an MA or as not an MA, and outputting the location of the MAs. Classifying the at least one candidate object as an MA comprises determining a probability that the at least one candidate object is an MA, and the method may further comprise outputting the probability of the at least one candidate object being an MA. Outputting the location or probability may comprise displaying the location or probability, or storing the location or probability with an identifier for the retinal image.

According to another aspect of the present invention, there is provided a computer readable storage medium arranged to store computer program instructions which, when executed on one or more processors, perform the method according to any one of the preceding claims.

An image processing apparatus comprising: a means for receiving a retinal image; and a processor for performing the method according to the first aspect.

The apparatus may further comprise a display for displaying the retinal image and/or the number of MAs.

The means for receiving a retinal image may comprise a communication unit for accessing a database.

The means for receiving a retinal image may comprise a camera.

The apparatus may be a mobile phone.

In other words, the present invention provides computer-aided detection of disease from eye images through generating output data providing an indication of the presence or absence of disease from at least one retinal image of a patient. The method can be used to detect disease indicated by the presence of objects within the eye, including, but not limited to the detection of diabetic retinopathy.

All features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE FIGURES

Embodiments of the present invention will now be described, by way of example only, with reference to the accompanying drawings, in which.

In the drawings, like reference numerals refer to like features throughout.

DETAILED DESCRIPTION

Figure 4:
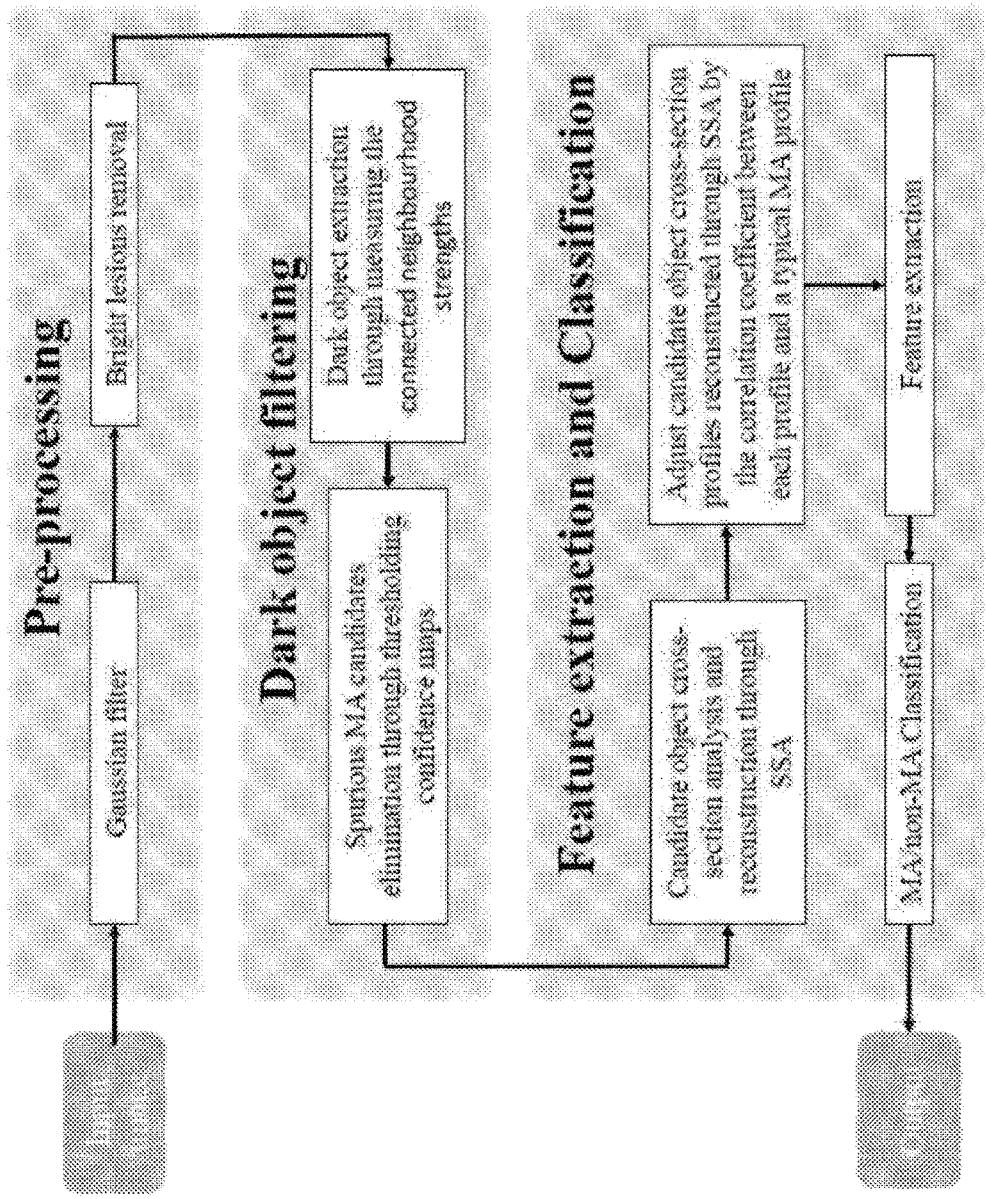
FIG. 4 shows a flow diagram of a method of analysing an image according to embodiments.

First, with reference to FIG. 4, the invention will be defined broadly before going into more detail in Section I. There are three main contributions to the method. First, a candidate extraction scheme is used to extract more MA candidates from eye images loaded into a computer program, including those close to vessels. Candidate objects are extracted through dark object filtering whereby connected neighbourhood strengths are measured, thus extracting a higher number of candidate objects. These candidates are then further filtered based on some criteria established from the candidate size and its relationship or its neighbouring regions.

Second, for every candidate, its cross-section profile along multiple directions, for example 12 directions, is obtained. Singular spectrum analysis (SSA) is used to decompose each profile and reconstruct a new one that does not have the influence of small noise. In other words, a new profile is constructed that is of a slow varying trend. The profile can be a sequence of the intensity value along the cross-section, or any other relevant information about the cross-section.

Third, each filtered profile is scaled using the correlation coefficient between itself and a typical true object cross-section profile (for example an ideal Gaussian shape assuming this candidate is a true MA). The measured correlation coefficient is used as a weight to adjust the shape of the candidate object cross-section profile so as to increase the difference between true and untrue candidates, thus enabling more accurate detection of disease. Statistical features of the cross-section profiles are used in classification to determine whether candidate objects are true objects, whereby true objects indicate a diseased state. In other words, this will enable an enhancement of the profiles in all directions for true MA candidates while decrease the similarity among profiles in all directions for non-MA candidates.

Images may be in a digital format or may be a scanned image. Images may be taken using a mobile device or a digital camera, with or without the use of an attachment. Images may also be received through an on-line system.

Objects include, but are not limited to, microaneurysms (MA), haemorrhages, blood vessels, scars and dark artefacts.

Eye images include, but are not limited to, retinal images including digital colour fundus images, digital greyscale fundus images, optical coherence tomograph images, digital scanning laser images including, but not limited to, ultra widefield images.

The method can differentiate other artefacts such as artefacts caused by defects within the imaging system, artefacts caused by defects within the lens of the camera, artefacts caused by dust on the lens of the camera or stray light in the imaging system. Such artefacts can be differentiated through dark object filtering and the artefact is therefore not extracted as a candidate object. Such artefacts may also be differentiated as a candidate object in the method. A threshold may be set for candidate size in the method dependent on the objects to be detected.

The method is a self-learning system, where machine learning is implemented through learning algorithms to enable automatic pattern recognition and intelligent decision making based on training sample images and/or data.

I PROPOSED METHOD

The proposed method is performed on the green channel of retinal images due to the fact that MAs, haemorrhages and vessels normally present the highest contrast against the surrounding background in this colour channel. However, the method may be performed on different colour channels of the images. MA detection is divided into preprocessing, candidate extraction through multilayered dark object filtering, candidate cross-section profile analysis based on SSA, feature extraction and classification. The details of these stages are provided in the following sections.

A. Image Preprocessing

Preprocessing attenuates the effects of noise and preserve the shape of true MAs. Pre-processing may be performed on different colour channels whereby a Gaussian filter is applied to different colour channels for filtering of the image. Preprocessing will now be described with reference to FIG. 5, where (a) is the green channel of the fundus image; (b) is the Gaussian filtered image of (a); (c) is the estimated background image $I_{bg}$; (d) is the shade correction image $I_{sc}$ that was accomplished by subtracting the median filtered image $I_{bg}$ from $I_{gg}$. The white regions are those pixels (such as bright lesions) brighter than their surrounding neighbours. The remaining pixels are processed for MA candidate extraction; and (e) is the preprocessed image $I_{pp}$ (the bright pixels in Igg indicated in $I_{sc}$ are replaced by the value of corresponding pixels in $I_{bg}$).

Figure 5:
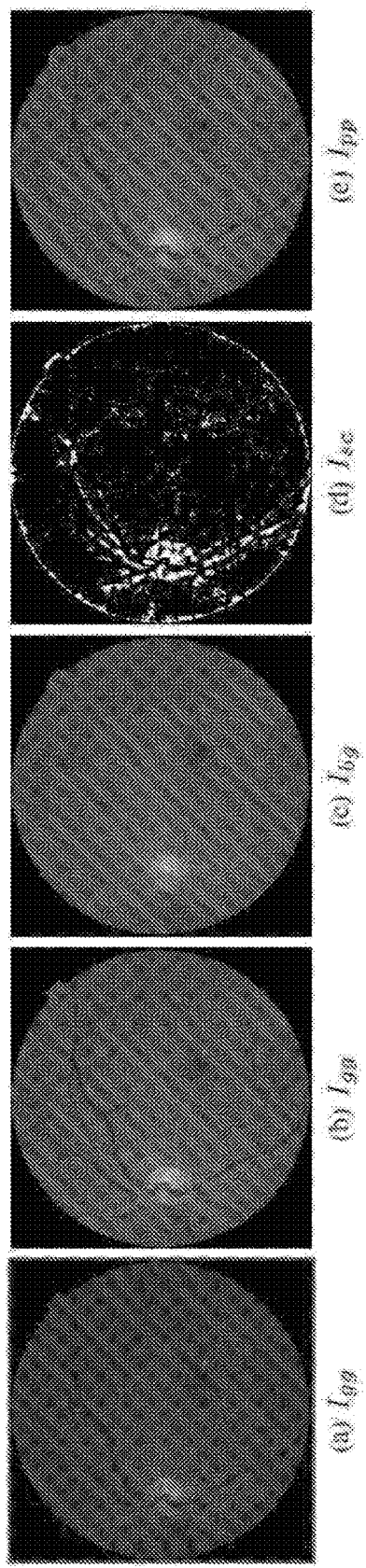
FIG. 5 shows the steps of image preprocessing according to embodiments.

Since the intensity profile of an MA usually follows the shape of an inverse Gaussian-like distribution, a Gaussian filter is applied to the green channel $I_g$ to enhance the small and dark structures, resulting in a filtered image $I_{gg}$ as shown in FIG. 5 (b). The Gaussian filter (width=3, variance=1) removes many structures occurring as a result of noise while leaving structures that correspond to MAs or vessels.

In addition, when bright lesions or regions are close together, the small gaps between them can be wrongly recognised as MAs in the later stages of the processing. In order to prevent these false positives (FPs), a shade correction algorithm is extended to remove any bright region from image $I_{gg}$. First, an estimated background image $I_{bg}$ (FIG. 5 (c)) is obtained by using a median filter (35×35) applied to $I_{gg}$. Subtracting $I_{bg}$ from $I_{gg}$ is then performed to obtain an image $I_{sc}$ (FIG. 5 (d)). Negative values in $I_{sc}$ indicate the corresponding pixels have a lower intensity, while pixels with a positive value have a higher intensity than their surrounding neighbours in $I_{gg}$. All pixels with a positive value in $I_{sc}$ are used to remove any bright region from image $I_{gg}$. The bright pixels in $I_{gg}$ are replaced by the values of their corresponding pixels in $I_{bg}$ resulting in the preprocessed image $I_{pp}$ (FIG. 5 (e)). Since this process removes bright regions (including bright lesions) from $I_{gg}$, it also removes the ambiguity when bright lesions or regions cluster together causing the gaps among them to be considered as MAs. Those pixels in $I_{sc}$ with a negative value are processed for candidate extraction in the next stage.

B. Candidate Extraction Using Multilayered Dark Object Filtering

Candidate extraction is a process which aims to identify any object in the image showing MA-like characteristics. These candidates will then be further analysed or classified into MAs and non-MAs. Previous reported approaches utilised different characteristics of MAs to extract MA candidates, including intensity-based and morphology-based methods. In an exemplary intensity-based method, a pixel is considered to be a possible local maximum (in the inverted image) if eight neighbouring pixels have lower or the same intensity. The use of these local maxima made it easier to obtain more MAs. However, it also brings in much more of the most common interfering structures such as vessel crossings as well as many local background regions due to high local intensity variation. Morphology-based methods employed a morphological top-hat transformation that eliminates the vasculature from a retinal image yet left possible MA candidates untouched. These methods were able to extract isolated MAs away from other dark objects including vessels. However, when an MA is close to other dark objects, they would be grouped into a larger object in the process which could miss the MA.

Figure 6:
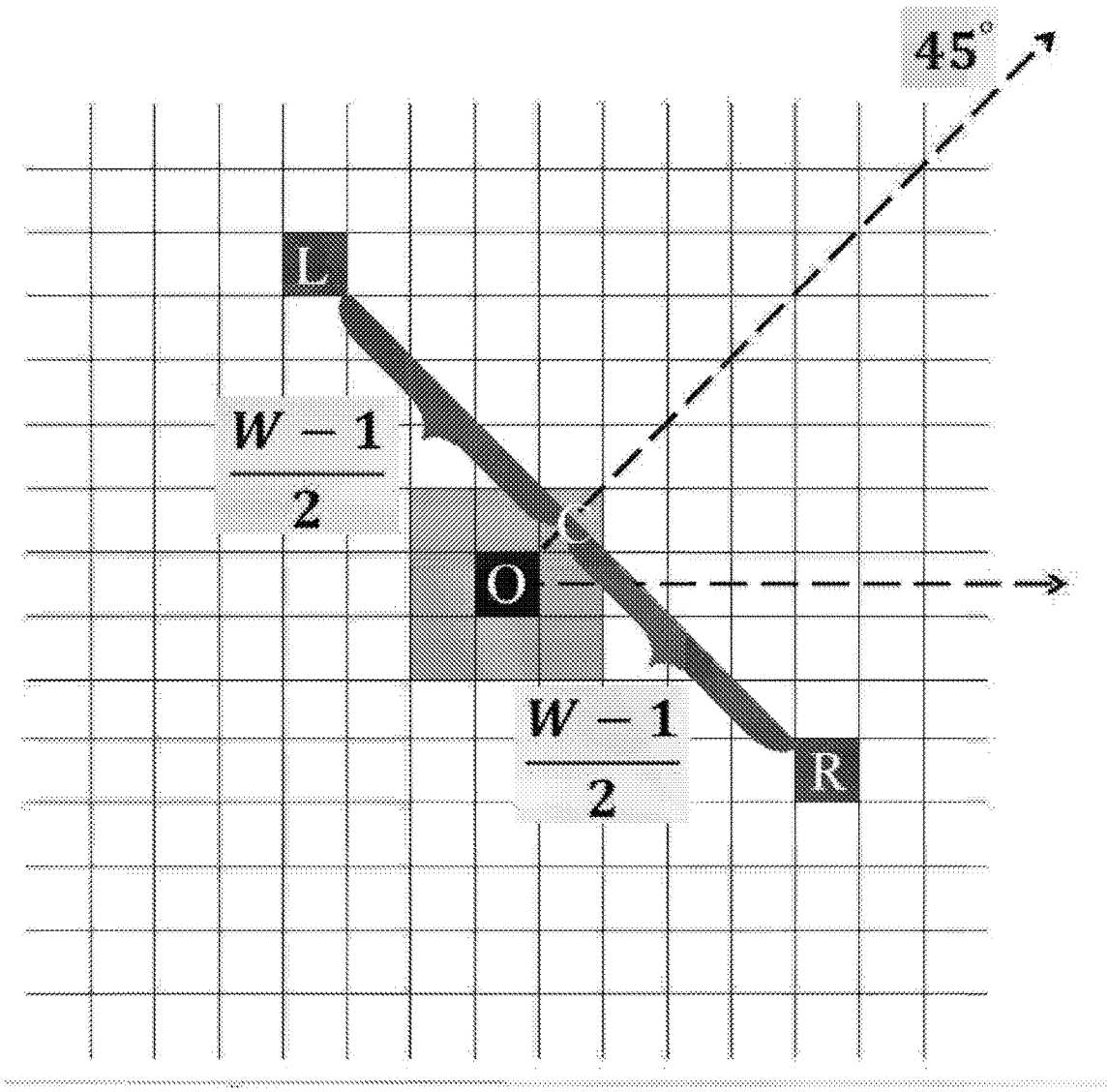
FIG. 6 illustrates the procedure for calculation of the connected neighbourhood strengths according to embodiments.

Embodiments described herein have largely addressed these limitations by using a multilayered dark object filtering method. After preprocessing, all pixels (x, y) with negative values in $I_{sc}$ are regarded as initial positions to look for dark objects in image $I_{pp}$, which include vessels, dark lesions and noise. We estimate the position of a given dark pixel (x, y) within a dark object by examining all its neighbours' darkness through calculating a connected neighbourhood strength, defined by Eq. (1), represented in FIG. 6.

$$p_i(x,y,\theta_i) = I_{gg}(x+(\cos\theta_i - w\sin\theta_i), y+(\sin\theta_i + w\cos\theta_i)) + I_{gg}(x+(\cos\theta_i + w\sin\theta_i), y+(\sin\theta_i - w\cos\theta_i)) - 2I_{gg}(x+\cos\theta_i, y+\sin\theta_i) \quad (1)$$

where $$w = \frac{(W-1)}{2},$$

w is the estimated width for the cross-section of dark objects. FIG. 6 illustrates the procedure for calculation of the connected neighbourhood strengths: p=I(L)+I(R)−2I(C), where I(x) is the intensity at pixel x; O is the current pixel; C is one of eight neighbourhood pixels; and L and R are pixels located $$\frac{(W-1)}{2}$$

pixels away from C in opposite directions. Note that the parameter p has a larger positive value when a pixel belongs to a dark object. In principle, the scale of W should be large enough so that L and R are outside the candidate objects. In our experiments, was set to 7 pixels. Since a dark object has lower values than its background, $p_i$ should have a positive value if the neighbour of pixel C is part of it. On the other hand, if the neighbouring pixel belongs to the background, $p_i$ should be close to zero or negative.

Figure 7:
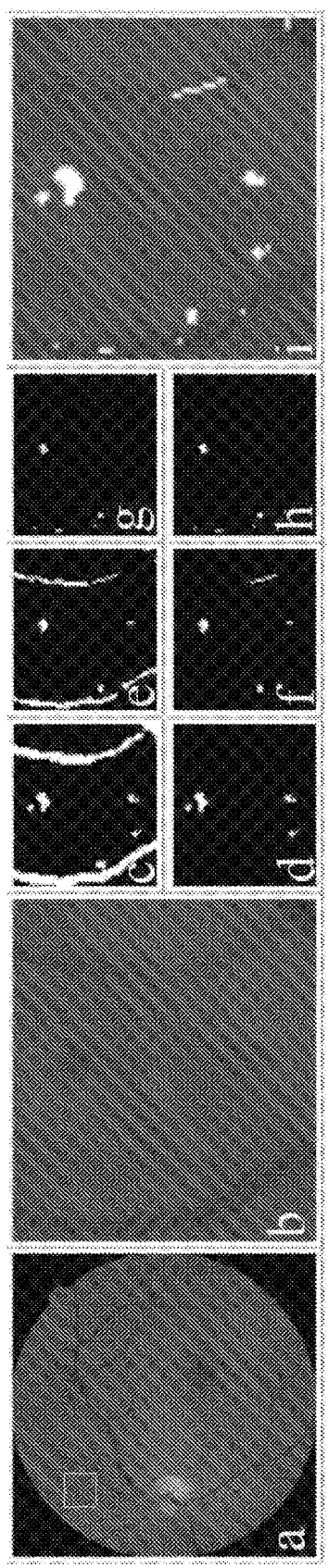
FIG. 7 shows the process of generating a confidence map according to embodiments.

All pixels (x, y) with negative values in $s_{sc}$ are processed sequentially according to Eq. (1) to produce a confidence map as described in Algorithm 1. FIG. 7 shows the process of generating a confidence map. (a) $I_{pp}$ (b) A part of $I_{pp}$; Sample confidence layers $M_j$: (c) M1, (e) M3, and (g) M5 for the same region in (b); (d), (f) and (h) are corresponding confidence layers after removing larger objects; (i) Final combined confidence map superimposed on (b).

In order to ensure only the pixels sufficiently darker than their background are chosen, the connected neighbourhood strength is thresholded (line 3, 6 in Algorithm 1 (shown later)). This threshold is denoted as δ=μ+kσ, where μ and σ are the mean and the standard deviation of the connected neighbourhood strengths of all pixels indicated by $I_{sc}$ with a negative value. In this study, k was fixed to 1.

As shown in lines 5-14 in Algorithm 1 (shown later), if a pixel has j neighbouring pixels that have strength greater than δ, it appears in layers 1 through j of the confidence map. If all neighbouring pixels' strengths have higher values than δ, the current pixel appears in all layers. On the other hand, if all its neighbours' strengths are lower than δ, this pixel cannot appear in any layer. During this process, $N_{x,y}$ is calculated (line 6) for each pixel (x, y). A higher $N_{x,y}$ value means pixel (x, y) has darker neighbours, i.e, the dark pixel (x, y) itself is more likely in the middle of a dark object. A lower $N_{x,y}$ means pixel (x, y) is more likely to be on the edge of a dark object. As the confidence layers $M_j$ are generated based on the number of connected dark neighbours, lower layers (lower j) such as that in FIG. 7 (c) (M1) contains more pixels at the edge of a large dark object including those true MAs right next to vessel network, which may have been merged into the larger dark object. Those isolated MAs away from the vessel network will easily be obtained at this layer. Higher layers (higher j, such as M5 in FIG. 7 (g)) contain more small candidates close to another dark object. However, these also include these small vessel fragments at the pixel level. In addition, since the local contrast of some MAs is very low compared to their surrounding background, they cannot appear in certain higher layers. FIGS. 7 (c), (e) and (g) show the instances of such confidence layers (j=1, 3 and 5). Each layer includes potential candidate objects and part of the vessel network. The dark pixel information in different layers complement each other and is combined in the final confidence map to extract a higher number of candidate objects.

Any candidate object in each layer that is too large to be an MA is removed (lines 16-21 in Algorithm 1 below). To determine a threshold (Δ=100) for this operation, an observation was made based on the observation on the lesions in the ground truth images from the training set. The remaining objects include a number of MAs and small vessel fragments (FIGS. 7 (d), (f) and (h)). To obtain a higher number of true positive candidates, all remaining objects in each layer are combined into a final map in the binary image $I_{bin}$. Then, all candidates in $I_{bin}$ are validated again and any connected component that is larger than Δ is removed. Integrating all layers can sufficiently reduce false MA candidates and extract more dark lesions located close to the vasculature. FIG. 7 (i) visualises all candidates when superimposing $I_{bin}$ on $I_{pp}$. The connected pixels on the map indicate positions of MA candidate objects. In this way, thresholding confidence maps can be used to reject spurious candidate objects.

| Algorithm 1 Multilayered dark object filtering |
|---|
| 1: Process all candidate pixels in $I_{pp}$ which are negative value in $I_{sc}$ |
| 2: For each pixel (x, y). calculate the strengths $p_i$ of its eight connected neighbours in $I_{pp}$ according to Eq. 1 |
| 3: Calculate the global threshold δ = μ + kσ |
| 4: Create 8 empty binary images as initial layers $M_j$ (j = 1 . . . 8) |
| 5: for each pixel (x, y) do |
| 6:    Count the number ($N_{x,y}$ = 0 . . . 8) of its neighbours whose strength $p_i$ is larger than δ |
| 7:    if $N_{x,y}$ > 0 then |
| 8:       for j = $N_{x,y}$; j >= 1; j - - do |
| 9:          Include the pixel (x, y) into the jth layer $M_j$ |
| 10:       end for |
| 11:    else |
| 12:       The pixel (x, y) cannot appear at any layer |
| 13:    end if |
| 14: end for |
| 15: Create another empty binary image as the final confidence map $I_{bin}$ |
| 16: for each individual layer $M_j$ (j = 1 . . . 8) do |
| 17:    Find connected components as candidate objects |
| 18:    if the size of a candidate object as smaller than Δ then |
| 19:       Add this candidate to the final confidence map $I_{bin}$ |
| 20:    end if |
| 21: end for |
| 22: Remove any object (connected component) in $I_{bin}$ that is greater than Δ |

In other embodiments a different method may be used to reject spurious candidate objects before proceeding to analyse the remaining candidate objects. For example, in some embodiments spurious candidate objects may be rejected using a classifier-based method such as a k-nearest neighbour method.

C. Extraction of SSA-Based Cross-Section Profiles

The candidate objects on the confidence map may include MAs and the most common interfering objects, such as vessel crossings, retinal haemorrhages and small vessel fragments. Since these extracted candidates indicate the positions of the actual objects, region growing techniques could be used to obtain the actual shape of the objects. However, this procedure can encroach into neighbouring MAs and other objects and it highly depends on the local threshold setup. To avoid this situation, we utilise the candidates' profiles to extract a set of statistical features that can discriminate true MAs from non-MAs.

Figure 8:
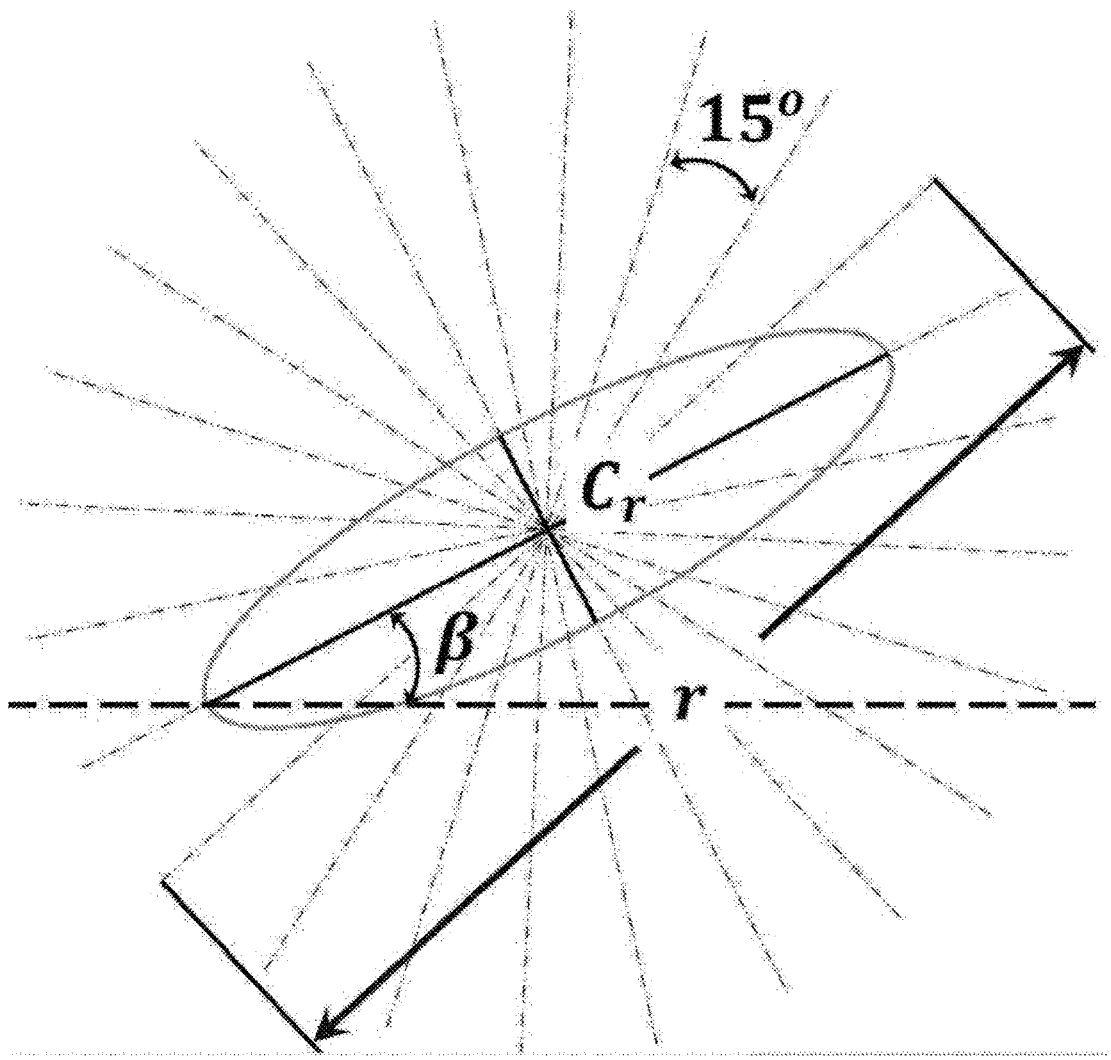
FIG. 8 illustrates how the cross-sections are established according to embodiments.

Work based on cross-sectional scanning of pixel intensities was been reported in prior art methods. A limitation in the published methods is that many small vessels or vessel crossings can lead to spurious MAs. Our proposed approach based on singular spectrum analysis has largely overcome this limitation by considering candidate objects' major axis when constructing their profiles. According to our observations, the major axis has significant difference in their profiles between circular structures (such as true MAs) and elongated structures (such as small vessels or vessel crossings). The different directions of cross-section lines can be denoted as:

$$\alpha[i] = \beta + \frac{180°}{n} \times i, i = 1, \ldots, n \quad (2)$$

where a[i] is the ith direction of the cross-section scanning lines, β is the angle between the major axis of the candidate object and x-axis and n is the total number of profiles to be generated. In our implementation, n was set empirically to 12. We do not need to consider extra directions of profiles, since this proposed approach can ensure that the cross-section lines contain the major axis and the minor axis of this object. FIG. 8 illustrates how the cross-sections are established.

The choice of cross-section length (r as indicated in FIG. 8) also affects the detection outcome. Through experimental observation, we choose r=31. Based on the above setup, we can obtain 12 sets of profiles of 31 pixels along 12 orientations for each candidate object. As shown in FIG. 8, there are 12 cross-section orientations for profile analysis. The length of pixels for each orientation is r. The ellipse is the candidate object; the solid black lines are the axes of the object and $C_r$ is its centroid. β equals to the angle between the horizontal line and the major axis of the candidate.

According to further embodiments, where the candidate object is elongated (such as a blood vessel), the intensity is measured along a row of vertically orientated cross-section lines. Alternatively, the intensity is measured along a row of horizontally orientated cross-section lines.

SSA is able to decompose these profile series and then reconstruct them in order to remove the noise and enhance meaningful signals. The main advantage of SSA over other subspace-based methods such as Principal Component Analysis (PCA) is that, the size of the generated Hankel matrix (as shown in eq. (3) below) can vary according to the expected number of underlying signal components, while this is fixed for PCA. Thus, a significantly better data decomposition into subspaces is achieved through SSA. After applying SSA, the key characteristics and the differences between the profiles of MAs and non-MAs are more prominent. A comparison of the different filtering methods is given in Section II. A brief description of the SSA technique follows. Two complementary steps of the basic SSA algorithm include decomposition and reconstruction.

1) Decomposition: This step consists of embedding operation and singular value decomposition (SVD). The cross-sectional intensity profile f with length r is mapped into an l×k matrix by applying the embedding operation:

$$X = [x_1, x_2, \ldots, x_k] = \begin{bmatrix} f_0 & f_1 & f_2 & \cdots & f_{k-1} \\ f_1 & f_2 & f_3 & \cdots & f_k \\ f_2 & f_3 & f_4 & \cdots & f_{k+1} \\ \vdots & \vdots & \vdots & \ddots & \vdots \\ f_{l-1} & f_l & f_{l+1} & \cdots & f_{r-1} \end{bmatrix} \quad (3)$$

where k=r−l+1, l denotes the window length (1≤l≤r). The trajectory matrix X is a Hankel matrix which has equal elements for all the diagonals i+j=constant, where i and j are indices of rows and columns. In our implementation, l was empirically set to half of r (l=15).

Then, the SVD of the trajectory matrix is created and represented as the sum of rank-one biorthogonal elementary matrices. Let $C_x=XX^T$ and assume $\lambda_1, \lambda_2, \ldots \lambda_l$ are the eigenvalues of covariance matrix $C_x$ in decreasing order ($\lambda_1 \geq \lambda_2 \geq \ldots \geq \lambda_l \geq 0$) and denote the corresponding eigenvectors by $u_1$ to $u_l$. If we denote $$v_i = \frac{X^T u_i}{\sqrt{\lambda_i}},$$

where the length of $v_i$ is 1×l, then, the SVD of the $C_x=XX^T$ is calculated. The collection ($\sqrt{\lambda_i}$, $u_i$, $v_i$) is considered as the ith eigentriple of SVD. The first few eigenvalues often carry the maximum energy of the data.

2) Reconstruction: In this step, the elementary matrices are firstly divided into a number of groups and summed the matrices within each group. The indices corresponding to the p eigenvalues of the desired component are defined as I={i, ..., i+p−1}. Then, let $\hat{X}_I = \Sigma_{j=i}^{i+p-1} X_j$ be the matrix corresponding to group I. Therefore, the overall sequence X can be written as $$X = \sum_{j=I_1}^{I_m} \hat{X}_j \quad (4)$$

where index m refers to the mth subgroup of eigentriples. The procedure for selection of the sets $I_1, \ldots, I_m$ is called eigentriple grouping. For a given group I, $$\frac{\sum_{i \in I} \lambda_i}{\sum_{i=1}^{l} \lambda_i}$$

is regarded as the contribution of the component $X_I$ in expansion (4). If we are to select all components to form one group, then the original series will be reconstructed. Using the obtained Hankel matrix, the cross-section profile can be reconstructed by diagonal averaging.

By application of SSA we can decompose the original data into a set of principal components (PCs). Our objective is to denoise and obtain the key profiles of MA candidates. Since the eigenvalues in the decomposition step are equal to the variance of the signal in the direction of their corresponding PCs, the smallest eigenvalues are regarded as noise and the largest eigenvalues belong to the signal subspace. After testing on many images, we observed that $\lambda_1 \gg \lambda_2$. Hence, we choose the first eigenvector $u_1$ for reconstruction.

Dark dots often appear at vessel junctions even where the vessels themselves are indistinct and also on vessels or haemorrhages where their contrast reaches a peak comparing to their surrounding background. In addition, small gaps may occur between bright areas and background noises (such as bright reflections) in fundus images. They are indistinguishable from MAs when interpreted too locally.

Figure 9:
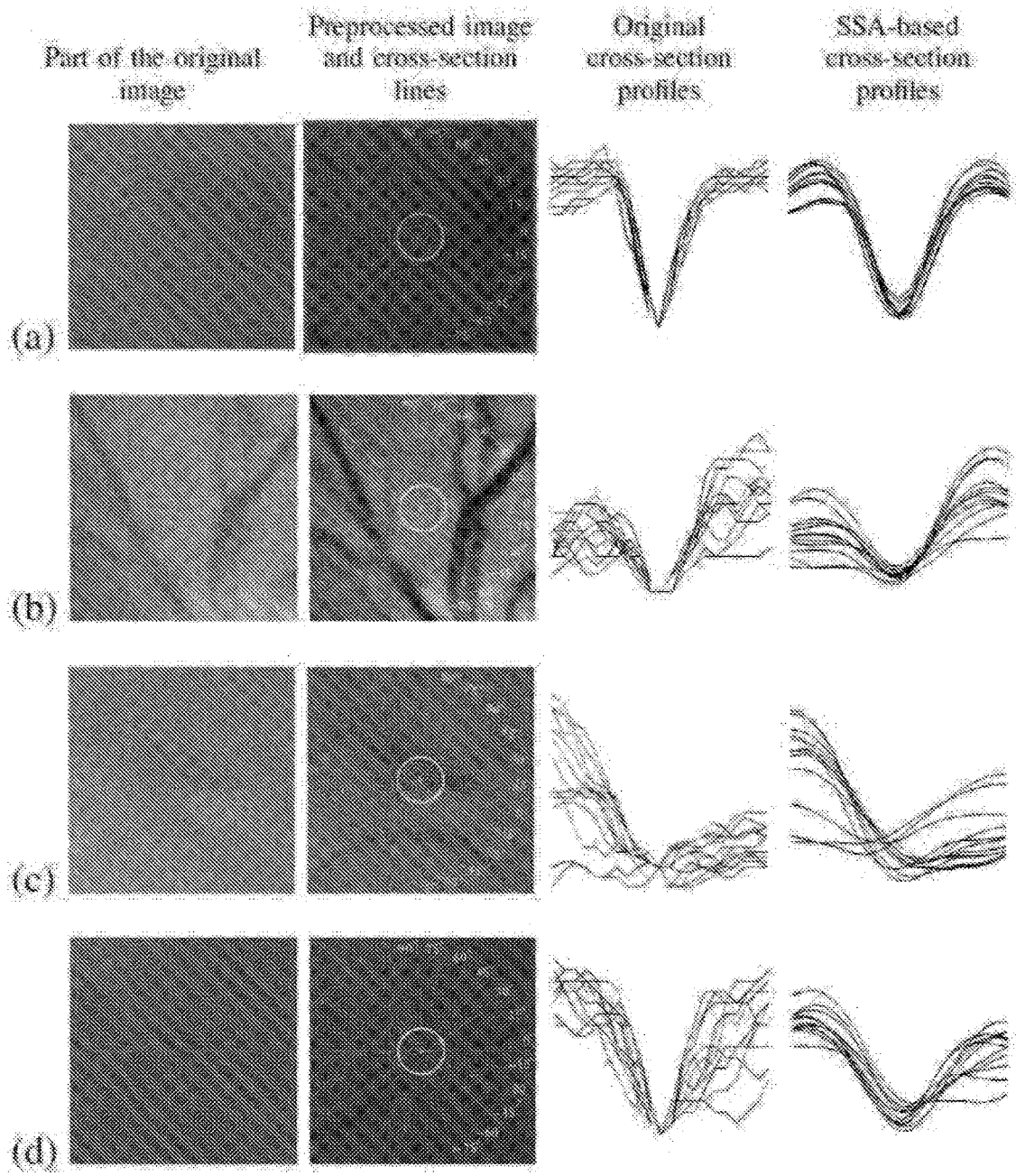
FIG. 9 shows the SSA-based scanning profile lines of different objects according to embodiments.

FIG. 9 shows the SSA-based scanning profile lines of an MA (a), a retinal background noise (b), an elongated structure (haemorrhage) (c) and a blood vessel crossing (d). The white circles in the middle of the subimages indicate the actual cross-section scanning regions with 31 pixel diameter. As shown in FIG. 9 (a), unlike these non-MA objects, the MA profiles show an obvious inverse Gaussian-like extremum in each orientation. Comparing profiles in FIGS. 9 (b), (c) and (d), the MAs can be discriminated from the most common interfering structures through analysing the respective sets of profiles of the candidate objects. FIGS. 9 (c) and (d) show that the extracted cross-sections contain the major and minor axes of the object. These filtered SSA profiles will provide the basis to extract the necessary features for classifying the candidate objects into MAs and non-MAs.

D. Feature Extraction and Classification System

As compared to those works that focused on pure pixel intensity profiles, SSA generated profiles further highlight the candidate object information and minimise the impact from the noise. After observing SSA-based profiles, we found the shapes of MA profiles are more similar in all orientations than those of non-MAs. In order to increase the difference between MAs and non-MAs, a dissimilarity score was assigned to each cross-section profile of a candidate object.

Figure 10:
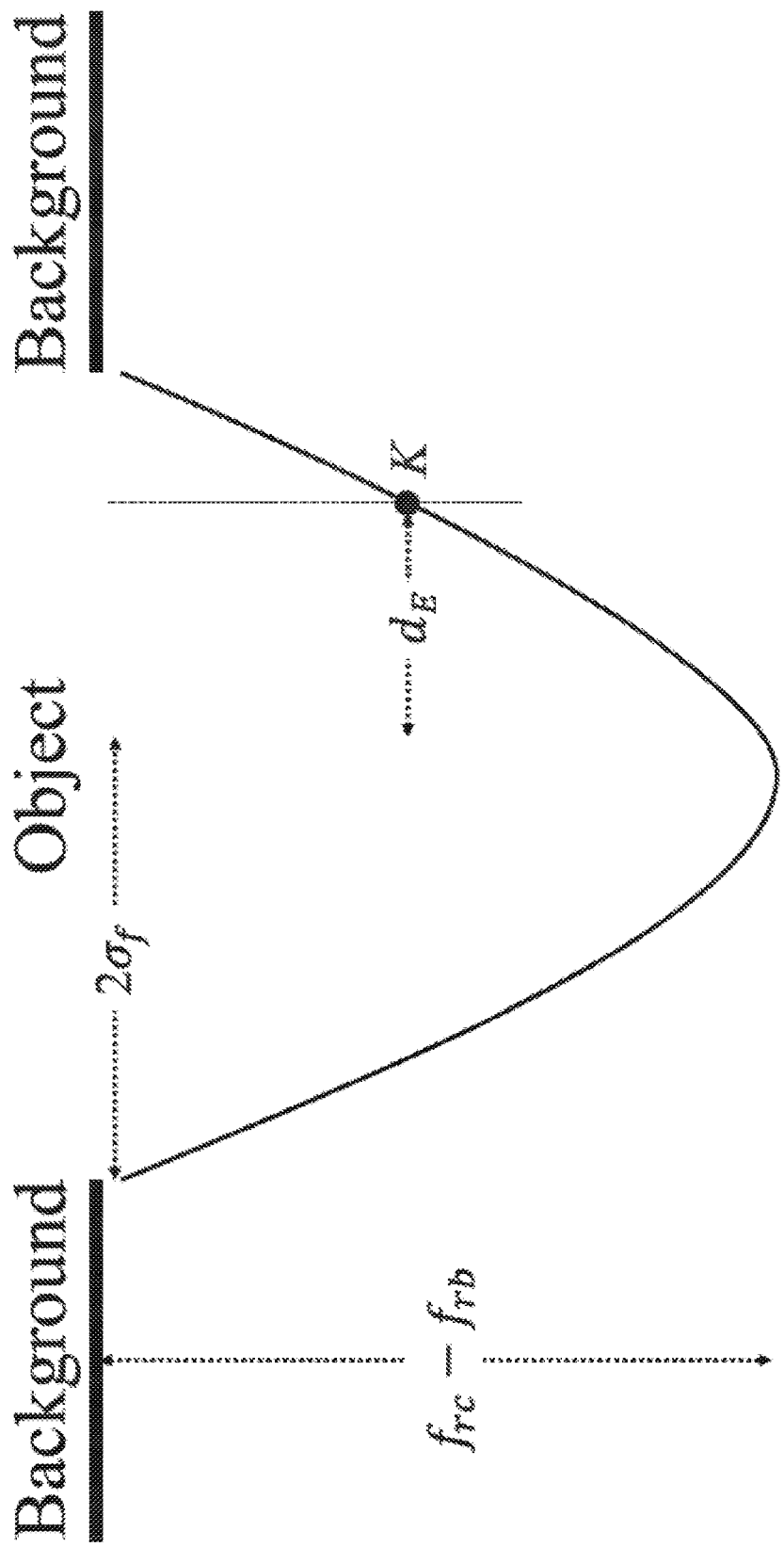
FIG. 10 shows an estimated intensity profile of a given MA candidate according to embodiments.

A correlation coefficient formula is used to calculate the dissimilarity score between an estimated MA profile and each of the 12 scanning profiles $f_r$. A Gaussian function is used to generate the estimated cross-section of MA which exhibits a Gaussian shape:

$$G = (f_{rc} - f_{rb})e^{\left(-\frac{d_E^2}{2\sigma_f^2}\right)} + f_{rb} \quad (5)$$

where $f_{rc}$ and $f_{rb}$ are the mean values of the pixel intensities of the region inside and outside the MA candidate in $I_{pp}$, $d_E$ is the distance between the centroid of the candidate region (local centre) and a current point K within the region, and $\sigma_f$ defines the spread of the estimated profile and is set to the value equal to half of the local candidate's radius. Therefore, $2\sigma_f$ is the radius of local candidate. An estimated intensity profile, having a Gaussian shape, of a given MA candidate is shown in FIG. 10. $f_{rc}$-$f_{rb}$ is the difference between the mean values of the pixel intensities of the region inside and outside the MA candidate in $I_{pp}$.

The correlation coefficient (cc) is then used to measure the similarity between an MA candidate and the Gaussian function. This value varies within [−1, 1]. The cc value will be high if the two profiles match well and vice versa. This means a true MA candidate will have high scores for its profiles along all cross-section directions, while non-MA candidates will have lower scores for at least some of its profiles in respective directions. The correlation coefficient is denoted as:

$$cc = \frac{\sum_i (f_r[i] - \bar{f}_r)(G[i] - \bar{G})}{\sqrt{\left(\sum_i (f_r[i] - \bar{f}_r)^2\right)\left(\sum_i (G[i] - \bar{G})^2\right)}} \quad (6)$$

where $\bar{f}_r$ and $\bar{G}$ are mean values of $f_r$ and G, and i is the pixel point along the profile scanning line i=1, 2, . . . , 31. Each cross-section profile $f_r$ is scaled by its own dissimilarity score (cc) and then a set of features is extracted from the new profile for classification. The scaled profile $f_d$ is determined by:

$$f_d[i] = \frac{f_r[i]}{cc}, i = 1, \ldots, 31. \quad (7)$$

Figure 11:
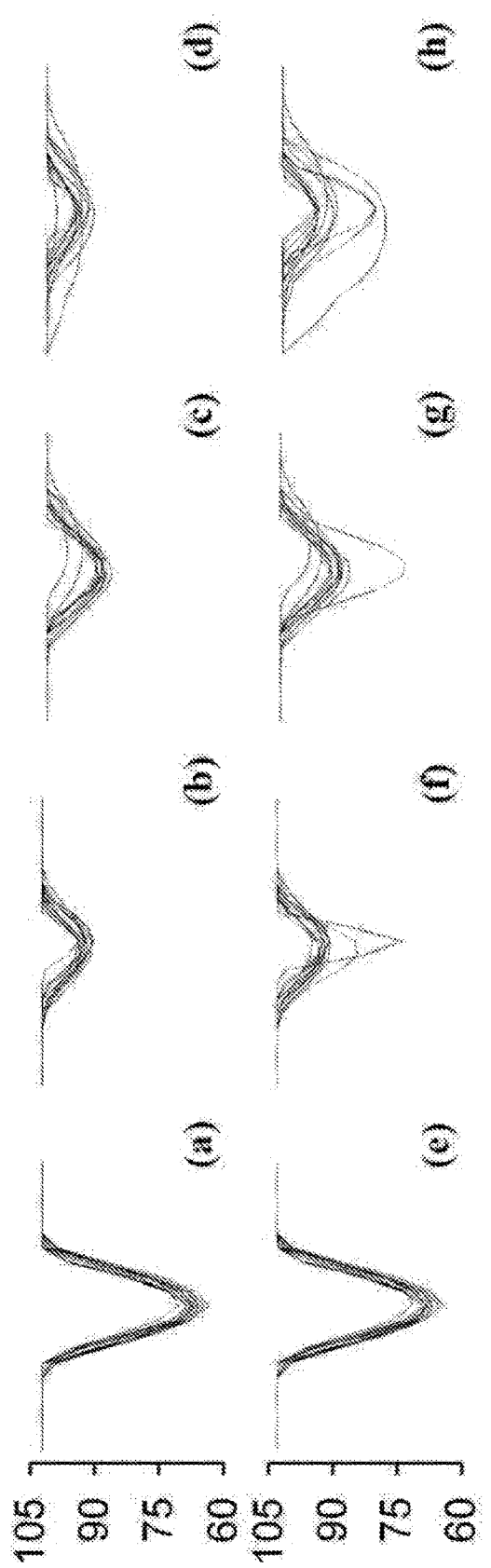
FIG. 11 shows a comparison of cross-section profiles with and without dissimilarity scores according to embodiments.

If the value of cc is close to 1, the scaled profile $f_d$ should be similar to the original profile $f_r$; otherwise, $f_d$ will become more different from $f_r$ if cc is close to zero or negative. These changes will enable the features to be more discriminating for classification of MAs and non-MAs. FIG. 11 shows the comparison between the cross-section profiles with and without being adjusted using their dissimilarity scores. (a) SSA-based profile of an MA, (b)-(d) SSA-based profiles of non-MAs, (e)-(h) SSA-based profiles with dissimilarity scores corresponding to (a)-(d). Comparing with the is original profiles (FIGS. 11 (b), (c) and (d)), the variations between adjusted profiles for the same object (FIGS. 11 (f), (g) and (h)) are larger for non-MA candidates. The changes of the profile directly impact the features for classification (see Section II for the classification performance with and without such dissimilarity scores).

Figure 12:
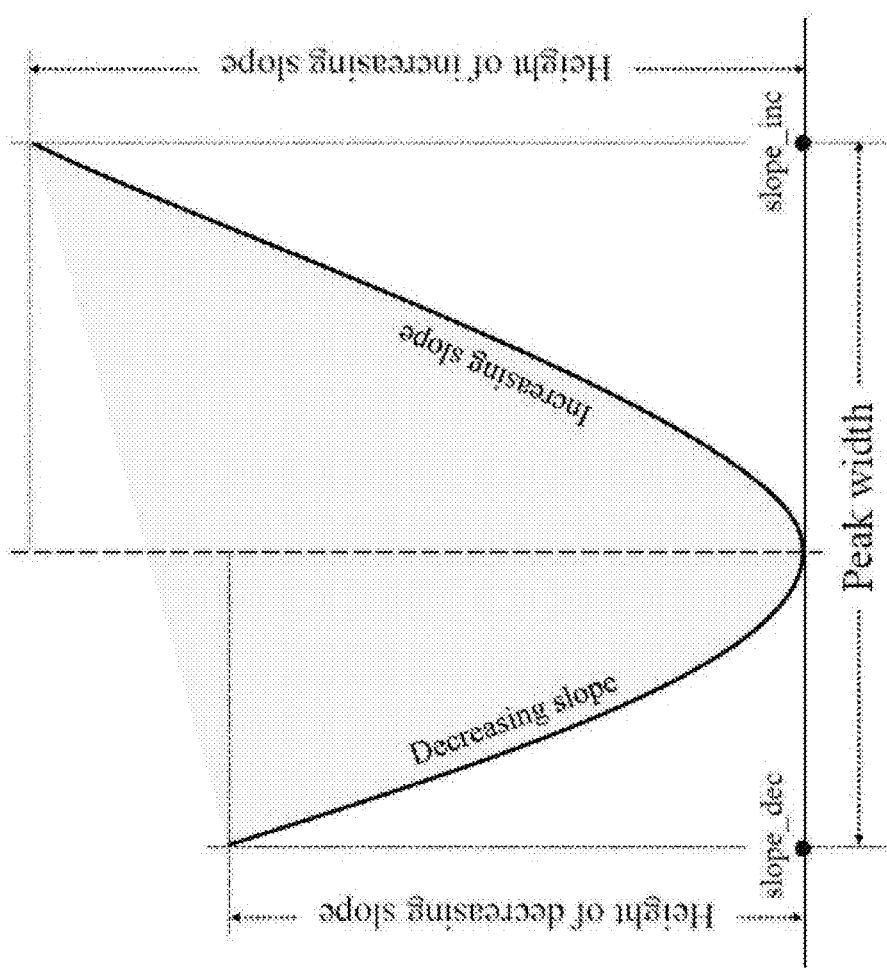
FIG. 12 illustrates a graphical interpretation of the slopes on a scaled profile.

Once the profiles have been scaled, the slopes are defined as either increasing or decreasing slopes based on whether the sign of the difference between sequential values of a profile is positive or negative. FIG. 12 illustrates a graphical interpretation of the slopes on a scaled sample profile. The peak width measures the spread of MA candidates in the considered orientation, denoted by $w_{peak}$=slope_inc−slope_dec. The values of slope_dec denote the start point of the decreasing slope, and slope_inc corresponds to the end points of the increasing slope. In total, ii features are extracted from the scaled profiles for classification, they are:

(1) The mean and standard deviation ($\mu_{w_{peak}}$ and $\sigma_{w_{peak}}$).

(2) The mean and standard deviation ($\mu_{h_{dec}}$ and $\sigma_{h_{dec}}$) of the heights of decreasing slopes of all cross-section profiles of the object.

(3) The mean and standard deviation ($\mu_{h_{inc}}$ and $\sigma_{h_{inc}}$) of the heights of increasing slopes of all cross-section profiles of the object.

(4) The compactness of an object is denoted as:

$$\sqrt{\frac{\sum_{j=1}^{n} d_j - \bar{d}}{n}},$$

where $d_j$ is the distance from its jth edge point of slope (slope_inc, slope_dec) to the centroid of the profile and $\bar{d}$ is the mean of the distance from each edge point to the centroid. Here n is the total number of edge points (n=24 in our implementation, as each candidate has 12 profiles, each profile has two edge pixels).

(5) The mean and standard deviation ($\mu_{\lambda_1}$ and $\sigma_{\lambda_1}$) of the largest eigenvalues of all profiles.

(6) The mean and standard deviation ($\mu_r$ and $\mu_r$) of aspect ratio, $$r = \frac{\lambda_1}{\lambda_2}.$$

and λ2 are tne respective value of the first and second largest eigenvalues of a profile.

Features (1)-(3) are typical properties of Gaussian shaped profiles. They give information about the sharpness and spread of the profiles and their difference from the surrounding regions. Compared with some published cross-sectional approaches, we added several new features. The compactness of an object (Feature (4)) is regarded as an extra shape feature to help remove elongated structures. Furthermore, some of the false positives come from the region of the optic disc. These MA-like structures have very high contrast in this region. Features (5) and (6) are used to remove these MA-like objects. The largest eigenvalue (Feature (5)) provides the object intensity level. Since the largest eigenvalue $\lambda_1$ contains most of the information and $\lambda_1 \gg \lambda_2$, the aspect ratio (Feature (6)) indicates that how much of the variation in a certain profile. This aspect ratio has a higher value for the true MAs. If the ratio has a lower value, the profile may contain small changes, such as the retinal background or the whole cross-section are inside of a large dark object. A detail of these feature vectors are given in Section II.

Using these features, we compared k-nearest neighbour (kNN), support vector machines (SVMs) and nave Bayes (NB) classifiers for classifying those candidates into true MAs and non-MAs. Our experiments showed that the kNN classifier gave the best performance. For the rest of the experiment, kNN is used as the main classifier. Details of the classifier comparison are provided in Section II. The final outputs of our proposed approach include a set of coordinates (in other words, locations) of detected MAs and their corresponding probabilities for being an MA. In some embodiments, the number of MAs is output. An MA is included in the number of MAs to be output if the probability of the candidate object being an MA is greater than a threshold.

II. EXPERIMENTS AND RESULTS

A. Setups

Figure 1:
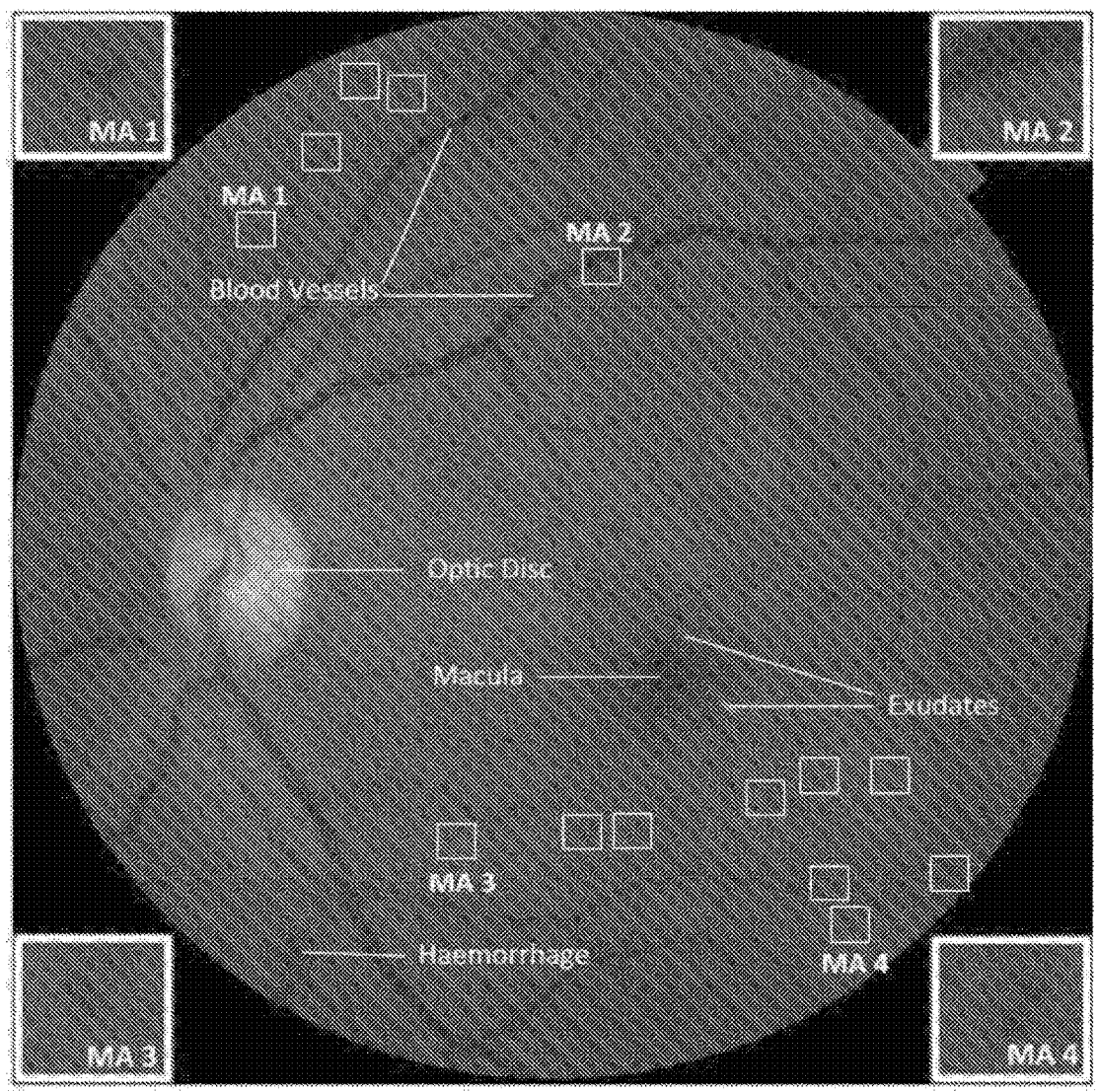
FIG. 1 is a digital fundus image.
Figure 2C:
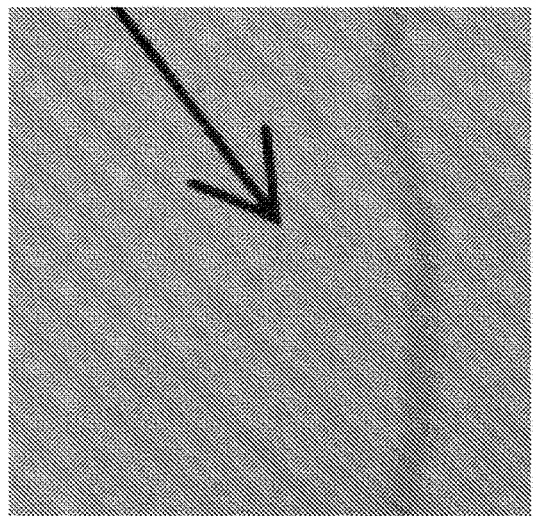
FIGS. 2a to 2c show examples of MAs and other blood vessels.
Figure 2B:
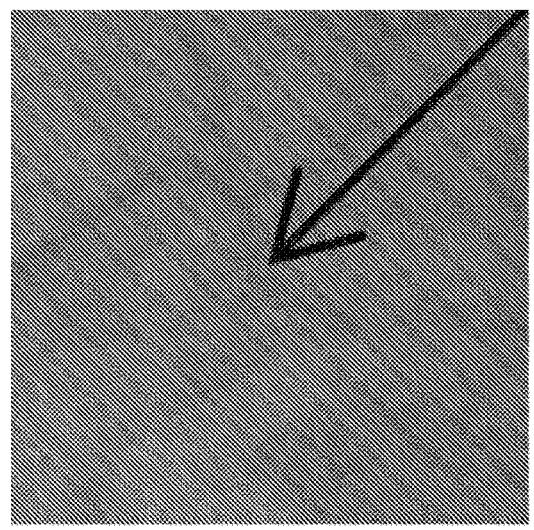
Figure 2A:
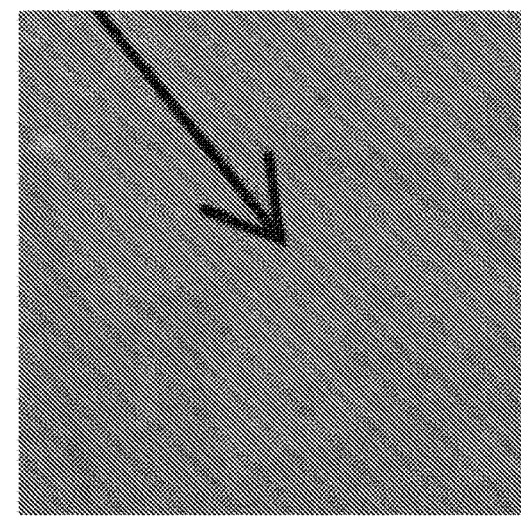
Figure 3:
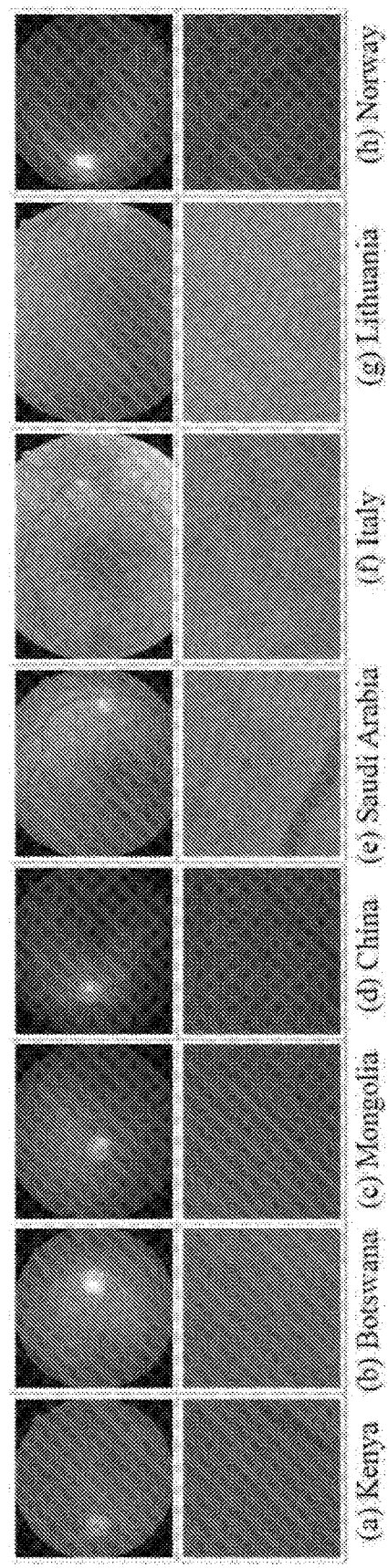
FIG. 3 shows retinal images from different populations.

In this work, we experimented on three sets of data, i.e. Retinopathy Online Challenge (ROC), DiaretDB1 2.1, and Moorfields Eye Hospital datasets. Images from different datasets were automatically resized and cropped by bilinear interpolation, to the same resolutions of those from the ROC dataset, either 768×576 (images of fundus with top and bottom parts missing and the diameter of the circular fundus region is approximately 800 pixels, such as FIGS. 3 (c), (e), (f), (g) and (h)) or 1389×1383 (full fundus images and the diameter of the circular fundus region is approximately 1300 pixels, such as FIGS. 3 (a), (b) and (d)). Despite their size and intensity variations, MAs are quite similar to each other.

We used 50 training images from the ROC to choose the parameters and classifier of our proposed method. While this public dataset has provided ground truth of MAs with their pixel coordinates, we had to manually prepare non-MA samples. The non-MA samples contain the previously presented false positives, such as vessel bifurcations and crossings, small disconnected vessels fragments and retinal haemorrhages. The training sets contain both true and false MA examples, including 336 MAs and 403 non-MA objects. We made observations on this dataset and noted the pixel properties of the key dark objects as shown in Table I. We used these size properties as standard reference for all processing. The following gives details of various experimental setups as well as additional experiments to justify some of our design choices.

In the preprocessing stage, in order to enhance the small and dark objects that correspond to MAs, the size of a Gaussian filter should be less than MAs diameter (5-10 pixels). In this study, the Gaussian filter (width=3, variance=1) is used. In principle, the size of the median filter should be wider than the widest vasculature in retinal images. It is set to 35×35 to estimate the background image $I_{bg}$ based on the observations in Table I.

After preprocessing, a confidence map is generated by using Algorithm 1. To find the optimal values for parameter W in Eq. (1) and k in Algorithm 1, the optimisation scheme is performed on the training set of the ROC. Each optimisation procedure is implemented on the 50 training images. Table II listed the first, second and third rank of the parameters based on the numbers of extracted candidate objects and missed true MAs. W=7 and k=1 give the least number of missed MAs. These values have been applied to all other experiments described in this paper. According to Table I, a size threshold Δ of 100 pixels was found to include all true MAs. Most of the vasculature will be removed in Algorithm 1 as their sizes are larger than 300 pixels, leaving the rest of candidates to be mostly small vessel fragments, small haemorrhages and true MAs.

During SSA, we need to decide the cross-section length r and window length l in Eq. (3). If r is too small, it is hard to distinguish MAs from haemorrhages and parts of the vasculature. Furthermore, large r results in increasing the computational time. We varied the value of r on the training data with all the odd numbers between 1 to 100 and found that 31 pixels gives consistent results. Selecting a proper window length l relies on a priori knowledge about the size characteristics of dark objects, such as MA, haemorrhages, retinal blood vessels and noises. With regards to l, a sufficiently large window length can effectively remove noise and preserve the original patterns of different objects.

Theoretically, l should not exceed $$\frac{r}{2}.$$

in our impremernauon, l was empirically set to half of the length of cross-sections (l=15). Based on l and the SVD of the trajectory matrix (15×15), we obtained 15 ordered eigentriples in the decomposition.

Figure 13:
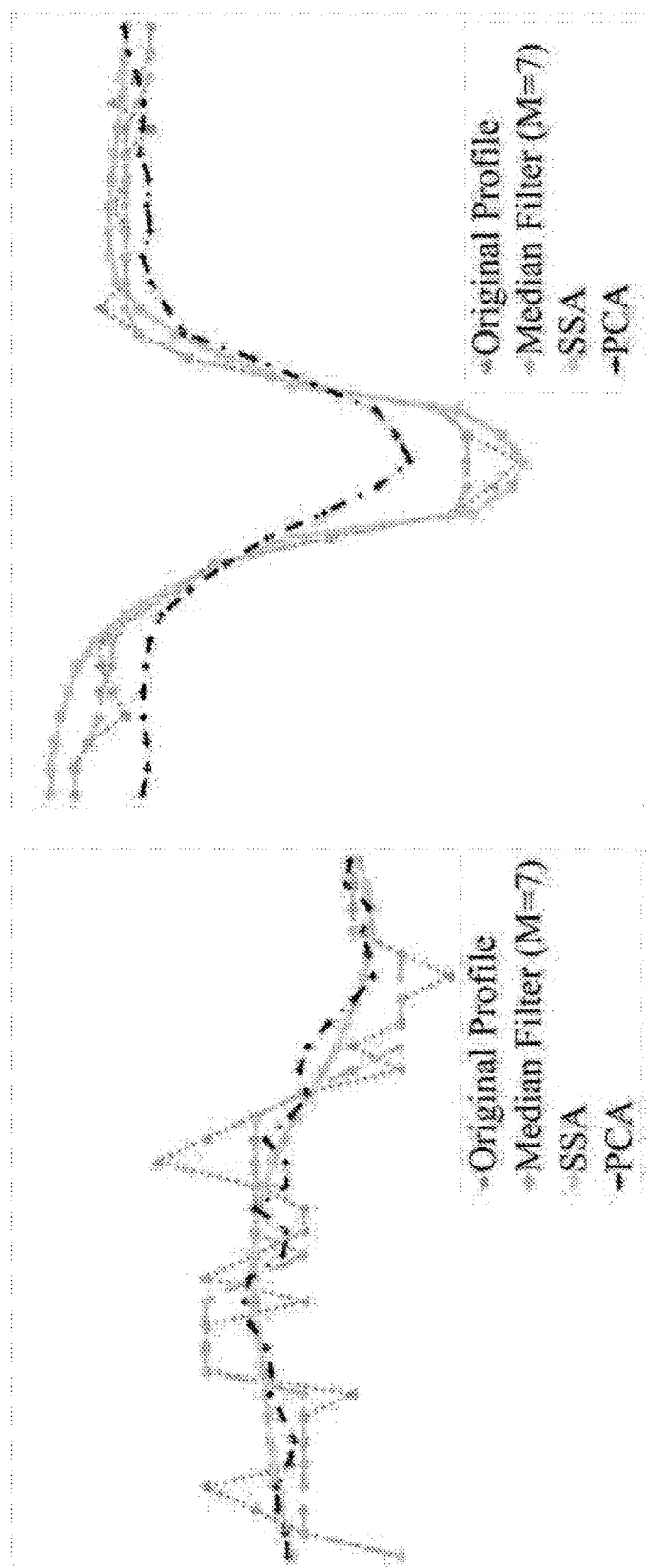
FIG. 13 shows a comparison between cross-sectional profiles according to embodiments.

The benefit of applying SSA is to obtain more smooth profiles and preserve the original patterns of different types of candidates. To demonstrate this, we compared SSA with other approaches of similar nature, such as median filters (with an optimal size M=7) and PCA. FIG. 13 visualises these approaches against the original intensity profile for smoothing two types of candidate profiles. In other words, FIG. 13 shows the comparison between the cross-section profiles of (a) a background and (b) an MA image for different approaches. Original profiles (line with triangles) include the majority of the local intensity variations. M is the size of median filter. SSA can generate smoother profiles and preserve the original patterns of candidate objects for retinal background and MA objects. Table III shows the sensitivities of various classifiers using different profiling approaches including using just original profiles at 1 FP/image. Original profiles may include many local intensity variations. In order to characterise the main signal and extract the features for classification, in the experiment we ignored very small changes in the original profile. We also implemented a thresholding method on the original profile to eliminate noise artefacts, including the minimum value of the absolute difference between consecutive values of the profile and the minimum value of the slope's height. The performance results based on the original profiles are shown in the first two columns in Table III. The filter size of the median filters is very sensitive to the intensity changes in candidate objects. Using small size cannot remove the noise and larger ones will lose MA pattern. In our experiment, we set the size of the median filter to 7 by using an optimisation scheme. In PCA, the first PC is used to reconstruct the candidate's profiles. However, it retains more noise (FIG. 13 (a)) and cannot fully represent object patterns (FIG. 13 (b)). As seen in Table III, the classification performance based on SSA outperformed the rest of profiling approaches.

It is not critical in terms of choosing any particular classification. In order to choose one for this work, we compared the performances of kNN, SVM and NB classifiers based on the features listed in Section I D. In this experiment, we used the training data in the ROC dataset as it contains 50 images with pixel based ground truth. Half of these images were used for training and the rest were used for testing. As seen from Table III, kNN outperformed the rest of the classifiers. In the following experiment, we use kNN for MA and non-MA classification. kNN has also higher computation speed on larger datasets. The benefit of using the proposed feature set is justified in the following evaluation on various datasets when comparing with other systems. An initial examination of the means and standard deviations of the feature vectors of all ROC training data are given in Table IV.

The full training data of the ROC and the parameter setups discussed in this section have been used in all evaluations as presented in the following section (no further training sets were added for any experiment).

B. Evaluation on Various Retinal Image Datasets

Figure 14:
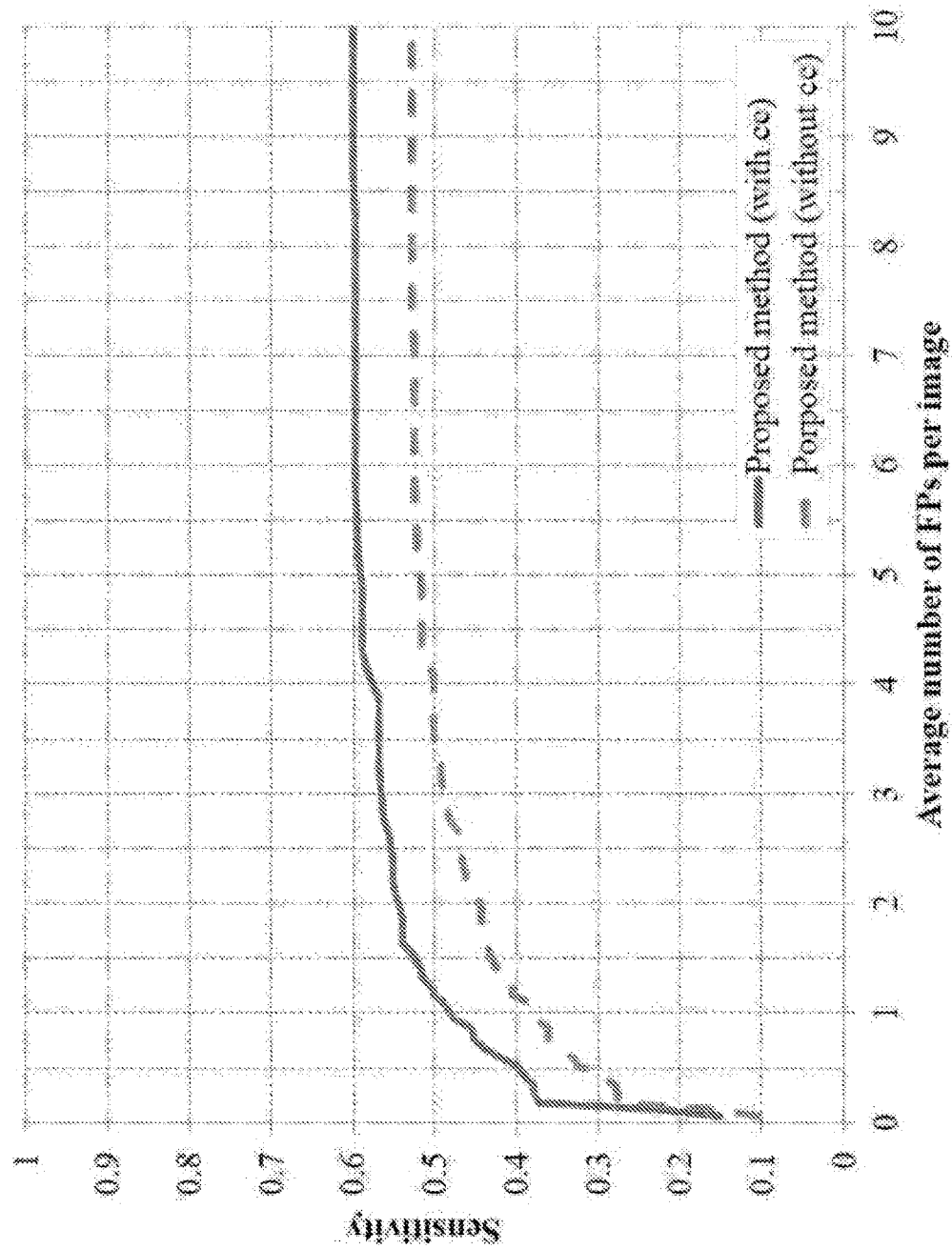
FIG. 14 shows the performance of embodiments of the present invention in MA detection with and without the use of correlation coefficient scores.

1) Retinopathy Online Challenge: The Retinopathy Online Challenge is to compare the capabilities of MA detectors under the same conditions. This dataset contains 50 training and 50 testing images, and all MAs were annotated by human experts. These images were acquired by three different cameras and had different resolutions and sizes, ranging from 768×576 to 1389×1383. The results of the proposed method are used to generate a free-response operating characteristic (FROC) curve which plots the sensitivity against average number of false positives (FP) per image. FIG. 14 demonstrates the performance of our proposed MA detection with and without the use of correlation coefficient scores. The final score is measured by the average sensitivity with seven predefined FPs per image (⅛, ¼, ½, 1, 2, 4, and 8 FP rate). The scores were measured independently by the Retinopathy Online Challenge team after we submitted our results on the testing data.

Table V shows the ranked results of the various methods submitted to the ROC. Our proposed method obtained an average score of 0.464, which is slightly higher than other published methods. Table VI shows the sensitivities at seven specific FP rates by our proposed method, an ensemble-based method and a cross-section based method. Our proposed method achieved higher sensitivity at low FP rates (1/8, 1/4, 1/2, 1 and 2 FPs/image), and our overall FROC score is slightly higher. Although the ensemble-based method achieved higher sensitivity at 4 and 8 false positives per image, the false positive rate of 1.08 FP/image is regarded as an indication of 'clinically acceptable' FP rate. Higher FP/image rates are not desirable in clinical practice.

Figure 15:
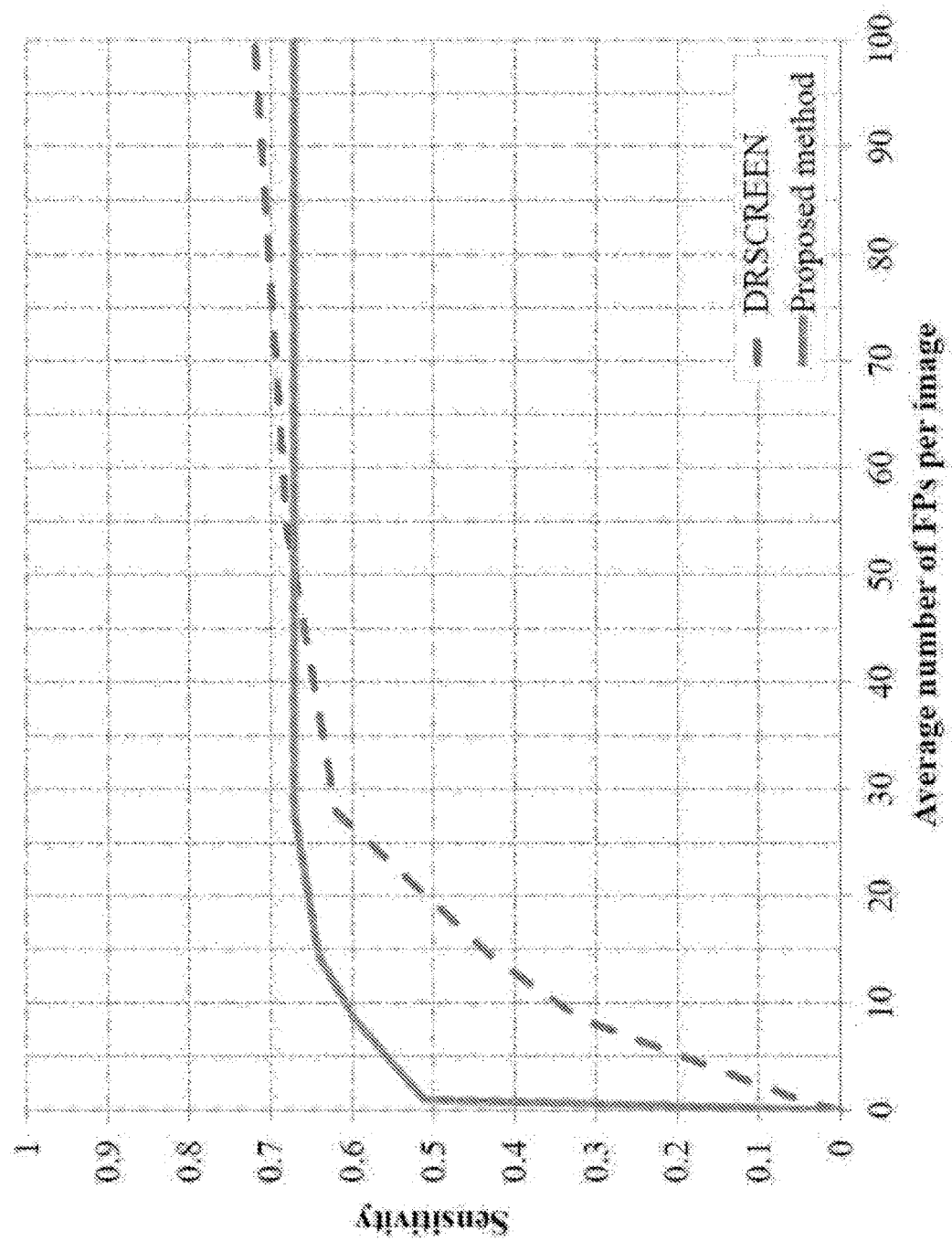
FIG. 15 shows a FROC curve for a dataset according to embodiments.

2) DiaretDB1 2.1 Dataset: Many factors can influence the performance of MA detection, such as their local contrast, colour and location. Our proposed method was further evaluated on different lesion categories in DiaretDB1 2.1 dataset. This dataset contains 89 uncompressed retinal images with 1500×1152 resolution. Each MA was assigned into a different lesion class (e.g., subtle, regular, obvious, in macula, near vessel or periphery). We used the same setup for the ROC dataset and tested all images. Table VII demonstrates the sensitivities of our proposed method (without and with a correlation coefficient) at 1 FP rate for various categories of MAs. It shows our proposed method can effectively recognise MAs. However, we still have lower performance on some categories (i.e., subtle and periphery). FIG. 15 shows the performance of our proposed method on the DiaretDB1 2.1 dataset, comparing with the ensemble-based method.

3) Dataset from Moorfields Eye Hospital: We tested the proposed method further on the dataset we collected from Moorfields Eye Hospital, London. The images originally came from different population based studies (such as Kenya (FIG. 3 (a), size: 3, 008×2,000, number: 9,587 images), Botswana (FIG. 3 (b), size: 3,456×2,304, number: 500 images), Mongolia (FIG. 3 (c), size: 3,888×2,592, number: 1,636 images), China (FIG. 3 (d), number: 579 images size: 1,380×1,180), Saudi Arabia (FIG. 3 (f), size: 4,288×2 848, number: 67 images), Italy (FIG. 3 (g), size: 1,024×1,024, number: 3,365 images), Lithuania (FIG. 3 (g), size: 3,072× 2,048, number: 4,962 images) and Norway (FIG. 3 (g), size: 2,196×1,958, number: 840 images)) and were anonymised to the point that nobody would be able to identify the individual patients. This anonymised dataset consists of 21, 536 retinal images. The images were then independently graded by human graders as normal or abnormal based on the presence or absence of MAs. In this work on the Moorfields Eye Hospital datasets, we used the same training data from the ROC and the same setups for testing on the ROC and DiaretDB1 2.1 datasets.

Figure 16:
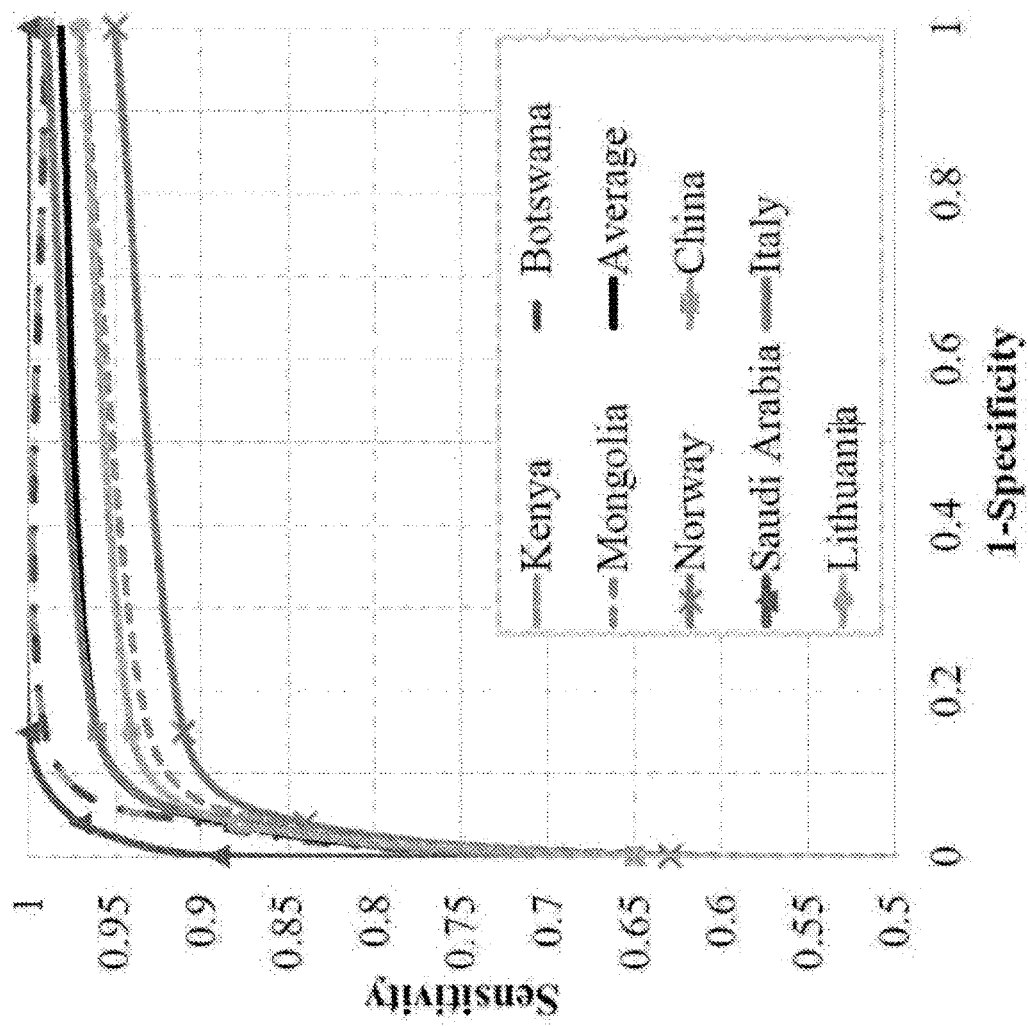
FIG. 16 shows a ROC curve for a dataset according to embodiments.

The test focused mainly on whether an image contains MAs or not. A receiver operating characteristic (ROC) curve analysis is able to evaluate this type of performance. We measured the sensitivity and specificity of the proposed MA detection:

$$\text{Sensitivity} = \frac{TP}{(TP + FN)}, \text{Specificity} = \frac{TN}{(TN + FP)},$$

where TP is true positive, FN is false negative, TN is true negative and FP is false positive. FIG. 16 shows the ROC curve of our presented approach for the eye hospital dataset. The average sensitivity and specificity can achieve 96.3% and 88.4% respectively. Table VIII shows the respective Kappa values (K) of different populations. K=1 means complete agreement and K=0 is no agreement. The strength of agreement is considered to be 'Good' if K is between 0.61-0.80.

C. Analysis of Misclassification

We review the FN images, i.e. those containing MAs in them but are labelled as normal. Most of these missed MAs are subtle, of low contrast, or having a blurry outline, so that their edges are not well defined against their background. Some of them are missed during the candidate extraction process, this aspect which should be improved in the future work. Even if they are extracted in this process, the SSA process may fail to establish prominent cross-section profiles. Detection of these subtle cases are also considered to be challenging for other existing approaches. A small number of FN cases are when MAs are located very closely to the vasculature. The multilayered confidence map is able to locate such MAs, however, the cross-section profile extraction process still needs to deal with the situation where the gaps between vasculature and the boundaries of MAs are extremely blurred. The classifier normally assigns such candidates with low probabilities as MAs due to the weak cross-section features. Furthermore, those MAs located around the periphery of fundus images are missed in the SSA process, because part of the profiles of these candidates locates outside the retinal region. We need to refine the SSA to address these issues. It may worth to as well add some similar examples to the training data for kNN. We also reviewed the FP cases which do not contain MAs but are labelled as abnormal. The proposed MA detector can discriminate MAs from vessel bifurcations and crossings. However, some of the FP cases are caused by detecting MA-like structures, including retinal pigmentation, dark artefacts and laser scars. Since their contrast with respect to their surrounding regions is high, they present Gaussian-like shape profiles which are very similar to actual MAs. Although false MAs do not affect patients' safety, they still need to be avoided in the MA detection. Integrating colour or shape-based analysis may help remove the excessive FP cases.

D. Discussion

The proposed candidate filtering process is able to significantly reduce the number of non-MA candidates and sufficiently extract more candidates located close to the vasculature. We take the advantage of a basic SSA method to filter MA candidates' profiles. In places where a single channel signal is available, SSA separates the data into its constituent components of different subspaces efficiently. Moreover, unlike other signal decomposition methods, here, by changing the embedding dimension a lower decomposition error (better noise restoration) is resulted. In our application, given the expected number of underlying components, SSA automatically decomposes and reconstructs each individual profile. These filtered profiles are then automatically scaled based on the correlation coefficient value to achieve more discriminative features for MAs and non-MA candidates. Based on the proposed set of features we achieved a robust detection of MAs on the data from various sources with different resolutions, quality and of different ethnic origins.

We examined our proposed algorithm using the ROC dataset. It obtained an overall slightly higher score than all other published methods, and achieved higher sensitivity at low FP rates (1/8, 1/4, 1/2, 1 and 2 FPs per image). With the DiaretDB1 2.1 dataset, we evaluated our method on different lesion categories. At the rate of 1 FP/Image which is clinically acceptable, our method can effectively recognise MAs from the most common categories. We have further evaluated our system on 21, 536 images provided by the Moorfields Eye Hospital. The results prove the robustness of our proposed approach, demonstrating a promising sensitivity and specificity when applied to larger datasets.

Although some vessel bifurcations and crossings are treated as MA candidates in the preprocessing stage, our proposed feature set is found to discriminate true MAs from those most common interfering candidate objects. Additionally, these features can be used to remove MA-like structures in the optic disc region without the detection of the optic disc first.

The processing time of our proposed method is approximately one minute, on a computer equipped with Intel Core i5 processor, running at 2.2 GHz. The method is currently implemented using MATLAB. This is much faster than our previous system, because a good number (around 50%) of false MA candidates are removed after the preprocessing stage.

III. CONCLUSION

In this work, we have demonstrated the scalability of our approach for localising MA in digital fundus images. Only a small number of image samples from the public domain were used for training (50 images) and the system was then tested on 21,536 previously unseen images. In our ongoing research project, we have been evaluating an automated system for retinal image analysis on very large datasets collected through diabetic retinopathy screening programmes and eye epidemiology studies from Africa, Asia (including Far East and Middle East countries) and Europe. The data used in this disclosure are from part of this project.

Our proposed MA detection achieved a good sensitivity and specificity on a per image basis. This is especially meaningful when this method is integrated into a reliable automated system for detecting abnormality in digital fundus images.

TABLE 1

THE DETAILS OF THE DETECTED CANDIDATE OBJECTS OF THE TRAINING SET

|  | MA | Haemorrhage | Connected vessels | others |
|---|---|---|---|---|
| Diameter | 5-10 pixels | any | 1-25 pixels | any |
| Area | <85 pixels | any | >300 pixels | any |

TABLE II

COMPARISON OF THE RESULTS OF CANDIDATE OBJECT EXTRACTION USING DIFFERENT VALUES OF W IN EQ. (1) AND k IN ALGORITHM 1

| W, k | Total number of extracted candidate objects | Number of true MAs that were missed (Percentage of 336 MAs) |
|---|---|---|
| 7, 1 | 3571 | 46 (13.7%) |
| 7, 1.2 | 3123 | 54(16.1%) |
| 5, 1.5 | 8456 | 55(16.4%) |

TABLE III

THE SENSITIVITIES OF VARIOUS CLASSIFIERS AT 1 FP/IMAGE BASED ON ORIGINAL PROFILES AND DIFFERENT SMOOTHED PROFILES (1 FP/IMAGE MEANS THE SENSITIVITY AGAINST 1 FALSE POSITIVE PER IMAGE, M IS THE SIZE OF MEDIAN FILTERS)

|  | Original profiles | Lazer and Hajdu's method | Median Filter (M = 7) | PCA | SSA |
|---|---|---|---|---|---|
| kNN (k = 15) | 0.1344 | 0.4154 | 0.3212 | 0.4045 | 0.4621 |
| SVM | 0.0934 | 0.3912 | 0.3011 | 0.3805 | 0.4461 |
| NB | 0.1143 | 0.3854 | 0.3151 | 0.3824 | 0.4470 |

TABLE IV

MEANS AND STANDARD DEVIATIONS OF THE FEATURES OF TRAINING VECTORS

| Feature | MA | | non-MA | |
|---|---|---|---|---|
| $\mu_{\omega_{peak}}$ | 8.2681 | 18.1765 | 2.6983 | 29.2812 |
| $\sigma_{\omega_{peak}}$ | 0.6208 | 2.8114 | 1.0810 | 7.4114 |
| $\mu_{h_{dec}}$ | 14.0625 | 27.4260 | 2.1623 | 50.1281 |
| $\sigma_{h_{dec}}$ | 0.5078 | 3.1649 | 0.2522 | 13.9563 |
| $\mu_{h_{inc}}$ | 15.0969 | 29.4434 | 1.2522 | 52.2541 |
| $\sigma_{h_{inc}}$ | 0.6259 | 4.4712 | 0.3122 | 14.1238 |
| $v$ | 0 | 1.3743 | 0.0469 | 3.7468 |
| $\mu_{\lambda_1}$ | 220.4479 | 376.1231 | 2.0593 | 1326.1231 |
| $\sigma_{\lambda_1}$ | 18.3845 | 50.8667 | 16.1147 | 188.9481 |
| $\mu_r$ | 3.4279 | 6.2223 | 1.1556 | 4.3148 |
| $\sigma_r$ | 1.0082 | 2.2382 | 1.8178 | 5.3178 |

TABLE V

RANKED RESULTS OF THE RETINOPATHY ONLINE CHALLENGE.

| | Team | Score |
|---|---|---|
| 1. | Our proposed method | 0.464 |
| 2. | DRSCREEN [31] | 0.434 |
| 3. | Lazer and Hajdu [24] | 0.424 |
| 4. | Z. Fegyver | 0.422 |
| 5. | Niemeijer et al. [19] | 0.395 |
| 6. | LaTIM [20] | 0.381 |
| 7. | ISMV [32] | 0.375 |
| 8. | OKmedical II. | 0.369 |
| 9. | OKmedical [22] | 0.357 |
| 10. | Lazer et al. [33] | 0.355 |
| 11. | GIB Valladolid [34] | 0.322 |
| 12. | Fujita Lab [35] | 0.310 |
| 13. | IRIA-Group [36] | 0.264 |
| 14. | Waikato Retinal Imaging Group | 0.206 |

TABLE VI

SENSITIVITIES OF THE DIFFERENT METHODS AT THE PREDEFINED FALSE POSITIVES PER IMAGE IN THE RETINOPATHY ONLINE CHALLENGE

| | 1/8 | 1/4 | 1/2 | 1 | 2 | 4 | 8 | Score |
|---|---|---|---|---|---|---|---|---|
| Our proposed method (with cc) | 0.273 | 0.379 | 0.398 | 0.481 | 0.545 | 0.576 | 0.598 | 0.464 |
| Our proposed method (without cc) | 0.191 | 0.277 | 0.327 | 0.397 | 0.463 | 0.507 | 0.528 | 0.384 |
| DRSCREEN [31] | 0.173 | 0.275 | 0.380 | 0.444 | 0.526 | 0.599 | 0.643 | 0.434 |
| Lazer and Hajdu [24] | 0.251 | 0.312 | 0.350 | 0.417 | 0.472 | 0.542 | 0.615 | 0.424 |

TABLE VII

SENSITIVITIES OF OUR PROPOSED METHOD AT 1 FP/IMAGE FOR ALL DIFFERENT CATEGORIES OF MAS.

| | Lesion category | DiaretDB1 | Proposed method (without correlation cofficient) | Proposed method (with correlation cofficient) |
|---|---|---|---|---|
| | MAs | 404 | 124 (30.7%) | 209 (51.7%) |
| Local contrast | Subtle | 133 | 5 (3.76%) | 38 (28.6%) |
| | Regular | 134 | 44 (32.8%) | 72 (53.7%) |
| | Obvious | 137 | 75 (54.7%) | 99 (72.3%) |
| Location | In macula | 8 | 1 (1.25%) | 2 (25.0%) |
| | Near vessel | 68 | 22 (32.4%) | 37 (54.4%) |
| | Periphery | 108 | 17 (15.7%) | 41 (38.0%) |
| | Other | 220 | 84 (38.2%) | 129 (58.6%) |

TABLE VIII

THE DIFFERENCES IN COHEN'S KAPPA COEFFICIENT (K) VALUES BETWEEN THE HUMAN GRADERS AND THE AUTOMATED SYSTEM ACROSS DIFFERENT RACIAL GROUPS.

| Racial Group | Kappa Value (K) | Standard Error of K | Confidence Interval | Strength of Agreement |
|---|---|---|---|---|
| Kenya | 0.752 | 0.01 | 0.731 to 0.772 | Good |
| Botswana | 0.758 | 0.033 | 0.694 to 0.822 | Good |
| Mongolia | 0.794 | 0.033 | 0.729 to 0.860 | Good |
| China | 0.740 | 0.024 | 0.693 to 0.787 | Good |
| Saudi Arabia | 0.930 | 0.026 | 0.879 to 0.981 | Very Good |
| Italy | 0.740 | 0.034 | 0.674 to 0.807 | Good |
| Lithuania | 0.746 | 0.034 | 0.680 to 0.812 | Good |
| Norway | 0.722 | 0.035 | 0.653 to 0.791 | Good |

According to embodiments of the present invention, candidate objects are first located by applying a dark object filtering process. Their cross-section profiles along multiple directions are processed through singular spectrum analysis. The correlation coefficient between each processed profile and a typical microaneurysm profile is measured and used as a scale factor to adjust the shape of the candidate profile. This is to increase the difference in their profiles between true microaneurysms and other non-microaneurysm candidates. A set of statistical features of those profiles is then extracted for a K-Nearest Neighbour classifier.

Experiments show that by applying this process, microaneurysms can be separated well from the retinal background, the most common interfering objects and artefacts. The results have demonstrated the robustness of the approach when testing on large scale datasets with clinically acceptable sensitivity and specificity.

The described approach in the evaluated system has great potential when used in an automated diabetic retinopathy screening tool or for large scale eye epidemiology studies.

Whilst certain embodiments of the invention have been described herein with reference to the drawings, it will be understood that many variations and modifications will be possible without departing from the scope of the invention as defined in the accompanying claims.

The invention claimed is:

1. An image analysis method, comprising:
receiving a retinal image;
identifying at least one candidate object from a plurality of objects within the retinal image;
for each identified candidate object, obtaining a plurality of cross-sectional profiles along a plurality of cross-sectional lines through the candidate object;
performing singular spectrum analysis SSA on the plurality of cross-sectional profiles for the candidate object, by using singular value decomposition SVD to decompose the plurality of cross-sectional profiles into a set of principal components and reconstructing a plurality of intensity profiles based on the principal components; and extracting at least one feature from the reconstructed intensity profiles for classification.

2. The method of claim 1, wherein identifying the at least one candidate object comprises dark object extraction through measuring connected neighbourhood strengths.

3. The method of claim 2, wherein identifying the at least one candidate object further comprises eliminating spurious candidate objects using thresholding confidence maps.

4. The method of claim 1, further comprising pre-processing the retinal image, wherein pre-processing comprises applying a filter to remove bright lesions.

5. The method of claim 4, wherein the filter is a Gaussian filter.

6. The method of claim 1, wherein the at least one candidate object comprises at least one of a microaneurysm MA, a blood vessel, a haemorrhage, or a scar.

7. The method of claim 6, wherein if the at least one candidate object comprises an MA, the at least one cross-sectional line comprises a plurality of cross-sectional lines spreading radially from the centre of the candidate object.

8. The method of claim 1, further comprising adjusting the at least one intensity profile of the candidate object by a correlation coefficient between the profile and a typical MA profile to obtain at least one scaled intensity profile for the candidate object.

9. The method of claim 8, wherein extracting at least one feature comprises measuring at least one of:
the mean of a peak width;
standard deviation of the peak width;
the mean of the heights of decreasing slopes of scaled intensity profiles along a plurality of cross-sectional lines through the candidate object;
the standard deviation of decreasing slopes of scaled intensity profiles along a plurality of cross-sectional lines through the candidate object;
the mean of the heights of increasing slopes of scaled intensity profiles along a plurality of cross-sectional lines through the candidate object;
the standard deviation of the heights of increasing slopes of scaled intensity profiles along a plurality of cross-sectional lines through the candidate object;
the compactness of the candidate object;
the mean of the largest eigenvalues of scaled intensity profiles along a plurality of cross-sectional lines through the candidate object;
the standard deviation of the largest eigenvalues of scaled intensity profiles along a plurality of cross-sectional lines through the candidate object;
the mean of the aspect ratio; and
the standard deviation of the aspect ratio.

10. The method of claim 1, further comprising classifying the at least one candidate object as an MA or as not an MA, and outputting the location of the MAs.

11. The method of claim 10, wherein classifying the at least one candidate object as an MA comprises determining a probability that the at least one candidate object is an MA, and the method further comprises outputting the probability of the at least one candidate object being an MA.

12. The method of claim 10, wherein outputting the location or probability comprises displaying the location or probability, or storing the location of the MA or probability with an identifier for the retinal image.

13. A computer readable storage medium arranged to store computer program instructions which, when executed on one or more processors, perform the method according to claim 1.

14. An image processing apparatus comprising:
a device for receiving a retinal image; and
a processor configured to:
identify at least one candidate object from a plurality of objects within the retinal image;
for each identified candidate object, obtain a plurality of cross-sectional profiles along a plurality of cross-sectional lines through the candidate object;
perform singular spectrum analysis SSA on the plurality of cross-sectional profiles for the candidate object, by using singular value decomposition SVD to decompose the plurality of cross-sectional profiles into a set of principal components and reconstructing a plurality of intensity profiles based on the principal components; and
extract at least one feature from the reconstructed intensity profiles for classification.

15. The apparatus of claim 14, further comprising a display for displaying either or both of the retinal image and the number of microaneurysms MAs.

16. The apparatus of claim 14, wherein the device for receiving a retinal image comprises a communication unit for accessing a database.

17. The apparatus of claim 14, wherein the device for receiving a retinal image comprises a camera.

18. The apparatus of claim 14, wherein the apparatus is a mobile phone.

19. An image processing apparatus comprising:
an input configured to receive a retinal image;
a candidate object analysis unit configured to identify at least one candidate object from a plurality of objects within the retinal image, obtain a plurality of cross-sectional profiles along a plurality of cross-sectional lines through the candidate object, for each identified candidate object, and perform singular spectrum analysis SSA on the plurality of cross-sectional profiles for the candidate object, by using singular value decomposition SVD to decompose the plurality of cross-sectional profiles into a set of principal components and reconstructing a plurality of intensity profiles based on the principal components; and
a feature extraction unit configured to extract at least one feature from the reconstructed intensity profiles for classification.

20. The image processing apparatus of claim 19, further comprising:
a pre-processing unit configured to pre-process the retinal image by applying a filter to remove bright lesions.

* * * * *